US009610387B2

(12) United States Patent
Hossainy et al.

(10) Patent No.: US 9,610,387 B2
(45) Date of Patent: Apr. 4, 2017

(54) PLASTICIZERS FOR A BIODEGRADABLE SCAFFOLDING AND METHODS OF FORMING SAME

(71) Applicant: ABBOTT CARDIOVASCULAR SYSTEMS INC., Santa Clara, CA (US)

(72) Inventors: Syed F. A. Hossainy, Hayward, CA (US); Stephen D. Pacetti, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 15/170,618

(22) Filed: Jun. 1, 2016

(65) Prior Publication Data

US 2017/0000930 A1 Jan. 5, 2017

Related U.S. Application Data

(63) Continuation of application No. 14/304,792, filed on Jun. 13, 2014, now Pat. No. 9,381,280.

(51) Int. Cl.
| | | |
|---|---|---|
| *C08G 63/00* | (2006.01) | |
| *A61L 31/14* | (2006.01) | |
| *A61L 31/06* | (2006.01) | |
| *C08J 3/18* | (2006.01) | |
| *C08K 5/00* | (2006.01) | |
| *B29C 45/72* | (2006.01) | |
| *C08G 63/02* | (2006.01) | |
| *B29K 67/00* | (2006.01) | |
| *B29L 31/00* | (2006.01) | |

(52) U.S. Cl.
CPC ............. *A61L 31/141* (2013.01); *A61L 31/06* (2013.01); *A61L 31/148* (2013.01); *B29C 45/72* (2013.01); *C08J 3/18* (2013.01); *C08K 5/0016* (2013.01); *A61L 2400/00* (2013.01); *B29K 2067/04* (2013.01); *B29L 2031/753* (2013.01); *C08J 2300/16* (2013.01)

(58) Field of Classification Search
CPC .............................. C08F 6/28; B29K 2067/00
USPC .... 528/271, 272, 336, 354, 480; 606/1, 213, 606/215, 228, 232; 623/1.11, 1.42, 1.43
See application file for complete search history.

(56) References Cited

U.S. PATENT DOCUMENTS

| | | |
|---|---|---|
| 2,037,197 A | 4/1936 | Huston |
| 2,158,107 A | 5/1939 | Carruthers |
| 2,260,295 A | 10/1941 | Carruthers |
| 2,350,388 A | 6/1944 | Claborn |
| 2,371,281 A | 3/1945 | Claborn |
| 2,461,372 A | 2/1949 | Collins |
| 2,752,328 A | 6/1956 | Magat |
| 2,917,410 A | 12/1959 | Vitalis |
| 2,958,364 A | 11/1960 | Thompson |
| 3,383,257 A | 5/1968 | James |
| 3,423,491 A | 1/1969 | McLain |
| 4,267,215 A | 5/1981 | Riggs |
| 5,085,629 A | 2/1992 | Goldberg |
| 5,403,897 A | 4/1995 | Ebato |
| 5,417,981 A | 5/1995 | Endo |
| 5,490,962 A | 2/1996 | Cima |
| 5,508,036 A | 4/1996 | Bakker |
| 5,581,387 A | 12/1996 | Cahill |
| 5,637,113 A | 6/1997 | Tartaglia |
| 5,707,329 A | 1/1998 | Pool |
| 5,834,582 A | 11/1998 | Sinclair |
| 5,868,781 A | 2/1999 | Killion |
| 5,980,972 A | 11/1999 | Ding |
| 5,981,694 A | 11/1999 | Gruber |
| 6,110,483 A | 8/2000 | Whitbourne |
| 6,114,653 A | 9/2000 | Gustafson |
| 6,131,266 A | 10/2000 | Saunders |
| 6,143,863 A | 11/2000 | Gruber |
| 6,153,252 A | 11/2000 | Hossainy |
| 6,350,009 B1 | 2/2002 | Freund |
| 6,475,779 B2 | 11/2002 | Mathiowitz |
| 6,547,994 B1 | 4/2003 | Monkhouse |
| 6,612,012 B2 | 9/2003 | Mitelberg |
| 6,865,810 B2 | 3/2005 | Stinson |
| 7,112,298 B2 | 9/2006 | Kampa |
| 7,163,715 B1 | 1/2007 | Kramer |
| 7,201,940 B1 | 4/2007 | Kramer |
| 7,229,471 B2 | 6/2007 | Gale |
| 7,311,980 B1 | 12/2007 | Hossainy |
| 7,517,353 B2 | 4/2009 | Weber |
| 7,540,997 B2 | 6/2009 | Stinson |
| 7,591,831 B2 | 9/2009 | Parsonage |
| 7,622,070 B2 | 11/2009 | Atladottir |
| 7,704,544 B2 | 4/2010 | Pacetti |
| 7,807,211 B2 | 10/2010 | Hossainy |
| 7,820,732 B2 | 10/2010 | Hossainy |
| 8,089,029 B2 | 1/2012 | Flanagan |

(Continued)

FOREIGN PATENT DOCUMENTS

| | | |
|---|---|---|
| WO | WO 2004/112863 A1 | 12/2004 |
| WO | WO 2007/142736 A2 | 12/2007 |
| WO | WO 2010/019478 A1 | 2/2010 |

OTHER PUBLICATIONS

Non-Final Rejection in U.S. Appl. No. 14/304,792, mailed on Jul. 31, 2015; 9 pages.
Notice of Allowance in U.S. Appl. No. 14/304,792, mailed on Nov. 12, 2015; 5 pages.
Supplemental Notice of Allowability in U.S. Appl. No. 14/304,792, mailed on Jun. 9, 2016; 2 pages.
International Search Report and Written Opinion of the International Searching Authority mailed on Nov. 9, 2015, for International Patent Application No. PCT/US2015/035171, 25 pp.
Cryogenic Grinding, http://en.wikipedia.org/wiki/Cryogenic_grinding, printed Sep. 17, 2014, 2 pages.
Molar Mass Distribution, http://en.wikipedia.org/wiki/Molar_mass_distribution, printed May 16, 2014, 4 pages.

(Continued)

*Primary Examiner* — Terressa Boykin
(74) *Attorney, Agent, or Firm* — Squire Patton Boggs (US) LLP

(57) ABSTRACT

Methods of making polymeric devices, such as stents, with one or more modifications such as addition of plasticizers, to improve processing, and the devices made by these methods.

19 Claims, 1 Drawing Sheet

(56) References Cited

U.S. PATENT DOCUMENTS

| | | |
|---|---|---|
| 8,221,822 B2 | 7/2012 | Flanagan |
| 8,281,737 B2 | 10/2012 | Austin |
| 8,481,138 B2 | 7/2013 | Miller |
| 8,496,865 B2 | 7/2013 | Wang |
| 8,524,148 B2 | 9/2013 | Shrivastava |
| 8,529,719 B2 | 9/2013 | Pingleton |
| 8,551,512 B2 | 10/2013 | Hossainy et al. |
| 8,563,103 B2 | 10/2013 | Hamann |
| 8,980,300 B2 | 3/2015 | Pacetti |
| 2001/0009769 A1 | 7/2001 | Williams |
| 2003/0059454 A1 | 3/2003 | Barry |
| 2003/0216804 A1 | 11/2003 | DeBeer |
| 2003/0236320 A1 | 12/2003 | Martin |
| 2004/0098100 A1 | 5/2004 | Williams |
| 2004/0106987 A1 | 6/2004 | Palasis |
| 2004/0143180 A1 | 7/2004 | Zhong |
| 2004/0167610 A1 | 8/2004 | Fleming, III |
| 2005/0112170 A1 | 5/2005 | Hossainy |
| 2005/0119720 A1 | 6/2005 | Gale |
| 2005/0131522 A1 | 6/2005 | Stinson |
| 2005/0147647 A1 | 7/2005 | Glauser |
| 2006/0111771 A1 | 5/2006 | Ton |
| 2006/0229711 A1 | 10/2006 | Yan |
| 2006/0241739 A1 | 10/2006 | Besselink |
| 2007/0142903 A1 | 6/2007 | Dave |
| 2007/0154512 A1 | 7/2007 | Dave |
| 2007/0179219 A1 | 8/2007 | Huang |
| 2007/0212547 A1 | 9/2007 | Fredrickson |
| 2007/0233277 A1 | 10/2007 | Yamamoto |
| 2008/0103584 A1 | 5/2008 | Su |
| 2009/0156772 A1 | 6/2009 | Strickler |
| 2009/0319028 A1 | 12/2009 | Ramzipoor |
| 2009/0319031 A1 | 12/2009 | Wang |
| 2010/0004734 A1 | 1/2010 | Ramzipoor |
| 2010/0096781 A1 | 4/2010 | Huang |
| 2010/0104734 A1 | 4/2010 | Orosa |
| 2010/0198331 A1 | 8/2010 | Rapoza |
| 2010/0262224 A1 | 10/2010 | Kleiner |
| 2012/0282392 A1 | 11/2012 | Sun |
| 2013/0041129 A1 | 2/2013 | Steichen |
| 2013/0115466 A1 | 5/2013 | Madsen |
| 2013/0150943 A1 | 6/2013 | Zheng |
| 2013/0216421 A1 | 8/2013 | Buckman |
| 2013/0289690 A1 | 10/2013 | Thapliyal |
| 2013/0331927 A1 | 12/2013 | Zheng |
| 2014/0011929 A1 | 1/2014 | Knoll |
| 2015/0150989 A1 | 6/2015 | Pacetti |
| 2015/0359647 A1 | 12/2015 | Pacetti |
| 2015/0359947 A1 | 12/2015 | Hossainy |

OTHER PUBLICATIONS

Sintering, http://en.wikipedia.org/wiki/Sintering, printed May 21, 2014, 15 pages.
Viscosity, http://en.wikipedia.org/wiki/Viscosity, printed Jun. 6, 2014, 24 pages.
Ansari, End-to-end tubal anastomosis using an absorbable stent (1979) *Fertility and Sterility* 32:197-201.
Ansari, Tubal Reanastomosis Using Absorbable Stent (1978) *International Journal of Fertility* 23:242-243, 2 pages.
Aoyagi et al., Preparation of cross-linked aliphatic polyester and application to thereto-responsive material (1994) *Journal of Controlled Release* 32:87-96, 10 pages.
Detweiler et al., Gastrointestinal Sutureless Anastomosis Using Fibrin Glue: Reinforcement of the Sliding Absorbable Intraluminal Nontoxic Stent and Development of a Stent Placement Device, *Journal of Investigative Surgery* (1996) 9:111-130, 20 pages.
Detweiler et al., Sliding, Absorbable, Reinforced Ring and an Axially Driven Stent Placement Device for Sutureless Fibrin Glue Gastrointestinal Anastomisis, *Journal of Investigative Surgery*, vol. 9(6), pp. 495-504 (Nov.-Dec. 1996), 10 pages.
Detweiler et al., Sutureless Anastomosis of the Small Intestine and the Colon in Pigs Using an Absorbable Intraluminal Stent and Fibrin Glue (1995) *Journal of Investigative Surgery* 8:129-140, 12 pages.
Detweiler et al., Sutureless Cholecystojejunostomy in Pigs Using an Absorbable Intraluminal Stent and Fibrin Glue (1996) *Journal of Investigative Surgery* 9:13-26, 14 pages.
He, Feng-Chun, et al., Assessment of Tissue Blood Flow Following Small Artery Welding with an Intraluminal Dissolvable Stent (1999) *Microsurgery* 19:148-152, 5 pages.
Filachione et al., Lactic Acid Derivatives as Plasticizers Esters of Polymeric Lactic Acid (1951) *Bur. Agric. and Ind. Chem.* 11:1-11, 20 pages.
Handbook of Pharmaceutical Excipients (2009) *Am. Pharm. Assoc.* pp. 215-222 (polyethylene glycol), 9 pages.
Helmus, Overview of Biomedical Materials (1991) *MRS Bulletin*, pp. 33-38, 6 pages.
Huang et al., Biodegradable Polymers Derived from Aminoacids (1999) *Macromol. Symp.* 144:7-32, 26 pages.
Inherent Viscosity vs Molecular Weight, Lactel Absorbable Polymers, http://www.absorbables.com/technical/inherent_viscosity. html, printed Nov. 14, 2014, 2 pages.
Katsarava et al., Amino Acid-Based Bioanalogous Polymers. Synthesis and Study of Regular Poly(ester amide)s Based on Bis(α-amino acid)α,ω-Alkylene Diesters, and Aliphatic Dicarboxylic Acids (1999) *Journal of Polymer Science, Part A: Polymer Chemistry*, 37:391-407, 17 pages.
Kelley et al., Totally Resorbable High-Strength Composite Material (1987) *Advances in Biomedical Polymers* 35:75-85, 11 pages.
Mauduit et al., Hydrolytic degradation of films prepared from blends of high and low molecular weight poly(DL-lactic acid)s (1996) *J. Biomed. Mater. Res.* 30:201-207, 7 pages.
Middleton et al., Synthetic biodegradable polymers as orthopedic devices (2000) *Biomaterials* 21:2335-2346, 12 pages.
Peng et al., Role of polymers in improving the results of stenting in coronary arteries (1996) *Biomaterials* 17:685-694, 10 pages.
Peuster et al., A novel approach to temporary stenting: degradable cardiovascular stents produced from corrodible metal-results results 6-18 months after implantation into New Zealand white rabbits (2001) *Heart* 86:563-569, 7 pages.
Phthalate, http://en.wikipedia.org/wiki/Phthalate, printed May 15, 2014, 21 pages.
Redman, Clinical Experience with Vasovasostomy Utilizing Absorbable Intravasal Stent (1982) *Urology* 20:59-61, 3 pages.
Rust et al., The Effect of Absorbable Stenting on Postoperative Stenosis of the Surgically Enlarged Maxillary Sinus Ostia in a Rabbit Animal Model (1996) *Archives of Otolaryngology* 122:1395-1397, 3 pages.
Saotome, et al., Novel Enzymatically Degradable Polymers Comprising α-Amino Acid, 1,2-Ethanediol, and Adipic Acid (1991) *Chemistry Letters* pp. 21-24, 4 pp.
Scapin et al., Use of triethylcitrate plasticizer in the production of poly-L-lactic acid implants with different degradation times (2003) *J. Mater. Sci.: Mater. In Med.* 14:635-640, 6 pages.
Seebach et al., Direct Degradation of the Biopolymer Poly[(R)-3-Hydroxybutyric Acid] to (r)-3-Hydroxybutanoic Acid and Its Methyl Ester, *Organic Syntheses*, Wiley 1983; CV 9:483, 5 pages.
Tamai et al., Initial and 6-Month Results of Biodegradable Poly-*l*-Lactic Acid Coronary Stents in Humans (2000) *Circulation*, 399-404, 6 pages.
Tsuji et al., Biodegradable Polymeric Stents (2001) *Current Interventional Cardiology Reports* 3:10-17, 8 pages.
Tsuji et al., Poly(L-lactide). IX. Hydrolysis in Acid Media (2002) *J. Appl. Polymer Science* 86:186-194, 9 pages.

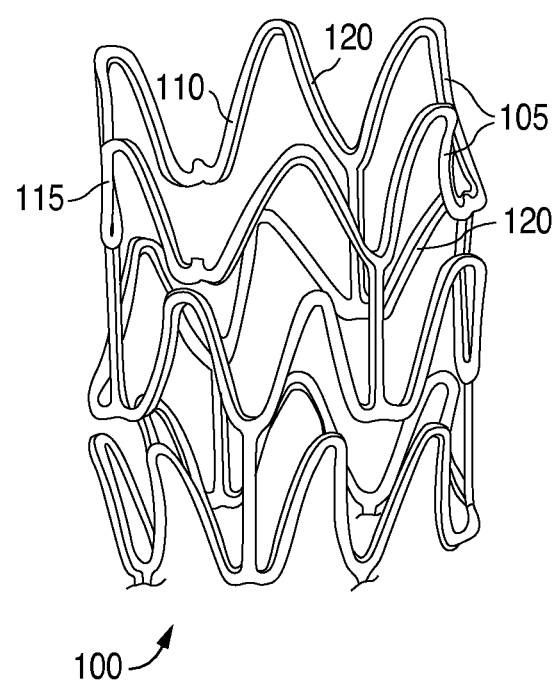

ated as U.S. Pat. No. 9,610,387 B2

PLASTICIZERS FOR A BIODEGRADABLE SCAFFOLDING AND METHODS OF FORMING SAME

CROSS-REFERENCE TO RELATED APPLICATION

This application is a continuation of co-pending U.S. application Ser. No. 14/304,792, filed on Jun. 13, 2014, published as United States Patent Application No. US 2015-0359947 A1 on Dec. 17, 2015, and issued as U.S. Pat. No. 9,381,280 B2 on Jul. 5, 2016, which is incorporated by reference herein in its entirety, expressly including any drawings, and is incorporated by reference herein for all purposes.

BACKGROUND

Field of the Invention

This invention relates to methods of manufacturing polymeric medical devices, in particular, stents, and especially stents used in the treatment of blood vessels.

Description of the State of the Art

Until the mid-1980s, the accepted treatment for atherosclerosis, i.e., narrowing of the coronary artery(ies) was by-pass surgery. While effective and evolved to a relatively high degree of safety for such an invasive procedure, by-pass surgery still involves potentially serious complications, and in the best of cases an extended recovery period.

With the advent of percutaneous transluminal coronary angioplasty (PTCA) in 1977, the scene changed dramatically. Using catheter techniques originally developed for heart exploration, inflatable balloons were employed to re-open occluded regions in arteries. The procedure was relatively non-invasive, took a relatively short time compared to by-pass surgery, and the recovery time was minimal. However, PTCA brought with it other problems such as vasospasm and elastic recoil of the stretched arterial wall which could undo much of what was accomplished and, in addition, it created a new disease, restenosis, the re-clogging of the treated artery due to neointimal hyperplasia.

The next improvement, advanced in the mid-1980s, was the use of a stent to maintain the luminal diameter after PTCA. This for all intents and purposes put an end to vasospasm and elastic recoil, but did not entirely resolve the issue of restenosis. That is, prior to the introduction of stents restenosis occurred in about 30-50% of patients undergoing PTCA. Stenting reduced this to about 15-20%, much improved but still more than desirable.

In 2003, drug-eluting stents or DESs were introduced. The drugs initially employed with the DES were cytostatic or cytotoxic compounds, that is, compounds that curtailed the proliferation of cells that contributed to restenosis. The occurrence of restenosis was thereby reduced to about 5-7%, a relatively acceptable figure. Thus, stents made from biostable or nonerodible materials, such as metals, have become the standard of care for percutaneous coronary intervention (PCI) as well as in peripheral applications, such as the superficial femoral artery (SFA), since such stents have been shown to be capable of preventing early and later recoil and restenosis.

However, a problem that arose with the advent of DESs was so-called "late stent thrombosis," the forming of blood clots long after the stent was in place. It was hypothesized that the formation of blood clots was most likely due to delayed healing, a side-effect of the use of cytostatic drugs. One potential solution is to make a stent from materials that erode or disintegrate through exposure to conditions within the body. Thus, erodible portions of the stent can disappear from the implant region after the treatment is completed, leaving a healed vessel. Stents fabricated from biodegradable, bioabsorbable, and/or bioerodable materials such as bioabsorbable polymers can be designed to completely erode only after the clinical need for them has ended. Like a durable stent, a biodegradable stent must meet time dependent mechanical requirements. For example, it must provide patency for a minimum time period.

Thus, there is a continuing need for biodegradable stents that meet both mechanical requirements, and methods of forming such stents.

SUMMARY OF THE INVENTION

Embodiments of the present invention include the following, without limitation, as described in the following numbered embodiments:

Embodiment [0001]

A method of fabricating a medical device, the method including, but not limited to including: providing a polymer; processing the polymer, optionally with another material, at a temperature above the melting temperature of the polymer, if the polymer exhibits a melting temperature above 35° C., or if the polymer does not exhibit a melting temperature above 35° C., at a temperature higher than (where "higher than" is at least 20° C., preferably at least 35° C., more preferably at least 50° C., and even more preferably at least 100° C.) the glass transition temperature ($T_g$), or 75° C., if 75° C. is greater than 100° C. above the $T_g$ of the polymer; adding a plasticizer to the polymer prior to, during, or both prior to and during the processing of the polymer at the above temperature ("melt processing operation"); optionally removing at least 60 weight % of the plasticizer from the processed polymer; optionally executing one or more additional processing operations to form a medical device from the processed polymer; and packaging the medical device.

Embodiment [0002]

In some embodiments, such as but not limited to that described in embodiment [0001], the medical device is subjected to a terminal sterilization process after packaging.

Embodiment [0003]

In some embodiments, such as but not limited to those described in embodiments [0001] and [0002], the plasticizer is added prior to the melt processing operation.

Embodiment [0004]

In some embodiments, such as but not limited to those described in embodiments [0001] and [0002], the plasticizer is added during the melt processing operation.

Embodiment [0005]

In some embodiments, such as but not limited to those described in embodiments [0001] and [0002], the plasticizer is added both prior to and during the melt processing operation.

Embodiment [0006]

In some embodiments, such as but not limited to those described in embodiments [0001]-[0005], the plasticizer is added at a weight ratio of plasticizer to polymer of about 1/5000 to about 1/9.

Embodiment [0007]

In some embodiments, such as but not limited to those described in embodiment [0006], the plasticizer is added at a weight ratio of plasticizer to polymer of about 1/2000 to about 1/15.

Embodiment [0008]

In some embodiments, such as but not limited to those described in embodiment [0006], the plasticizer is added at a weight ratio of plasticizer to polymer of about 1/1000 to about 1/20.

Embodiment [0009]

In some embodiments, such as but not limited to those described in embodiment [0006], the plasticizer is added at a weight ratio of plasticizer to polymer of about 1/500 to about 1/25.

Embodiment [0010]

In some embodiments, such as but not limited to those described in embodiment [0006], the plasticizer is added at a weight ratio of plasticizer to polymer of about 1/200 to about 1/35.

Embodiment [0011]

In some embodiments, such as but not limited to those described in embodiment [0006], wherein the plasticizer is added at a weight ratio of plasticizer to polymer of about 1/175 to 1/40.

Embodiment [0012]

In some embodiments, such as but not limited to those described in embodiments [0001]-[0005], the plasticizer is added in a sufficient amount to lower the glass transition temperature of the polymer by at least 5° C., by at least 10° C., by at least 15° C., or by at least 20° C., but not more than 75° C.

Embodiment [0013]

In some embodiments, such as but not limited to those described in embodiments [0001]-[0005], the plasticizer is added in a sufficient amount to lower the glass transition temperature of the polymer by 5° C. to 50° C.

Embodiment [0014]

In some embodiments, such as but not limited to those described in embodiments [0001]-[0005], the plasticizer is added in a sufficient amount to lower the glass transition temperature of the polymer by 10° C. to 40° C.

Embodiment [0015]

In some embodiments, such as but not limited to those described in embodiments [0012]-[0014], the sufficient amount is a weight ratio of plasticizer to polymer in the range from 1/50 to 1/3.

Embodiment [0016]

In some embodiments, such as but not limited to those described in embodiments [0001]-[0015], the melt processing operation comprises extrusion, injection molding, or a combination thereof.

Embodiment [0017]

In some embodiments, such as but not limited to those described in embodiments [0001]-[0016], at least one additional processing operation is executed, the at least one additional processing operation comprising heating the polymer to a temperature between the glass transition temperature or at least 28° C., if the glass transition temperature is lower than 25° C., and the melting temperature of the polymer, if the polymer has a melting temperature above 28° C., or if the polymer does not have a melting temperature above 28° C., the temperature that is 75° C. greater than the glass transition temperature, or 60° C., whichever is higher.

Embodiment [0018]

In some embodiments, such as but not limited to those described in embodiments [0001]-[0017], the melt processing operation comprises extrusion, injection molding, or a combination thereof to form a polymer tube, and at least one additional processing operation is executed, the at least one additional processing operation comprising heating the polymer to a temperature between the glass transition temperature, or at least 28° C., if the glass transition temperature is lower than 25° C., and the melting temperature of the polymer of the polymer tube, if the polymer has a melting temperature above 28° C., or if the polymer does not have a melting temperature above 28° C., the temperature that is 75° C. greater than the glass transition temperature, or 60° C., whichever is higher.

Embodiment [0019]

In some embodiments, such as but not limited to those described in embodiments [0018], the at least one additional processing operation during which the heating occurs comprises axial expansion of the polymer tube, radial expansion of the polymer tube, or a combination of radial and axial expansion of the polymer tube.

Embodiment [0020]

In some embodiments, such as but not limited to those described in embodiment [0019], the tube is radially and axially expanded sequentially.

Embodiment [0021]

In some embodiments, such as but not limited to those described in embodiment [0019], the tube is radially and axially expanded at least partially concurrently.

Embodiment [0022]

In some embodiments, such as but not limited to those described in embodiments [0018]-[0021], the method additionally comprises forming a pattern in the tube to form the medical device.

Embodiment [0023]

In some embodiments, such as but not limited to those described in embodiment [0022], forming a pattern comprising laser cutting.

Embodiment [0024]

In some embodiments, such as but not limited to that described in embodiments [0001]-[0023], the optional removal of the plasticizer is not executed, and at least 50 weight % of the plasticizer that was added remains in the medical device that is packaged.

Embodiment [0025]

In some embodiments, such as but not limited to that described in embodiment [0024], the plasticizer is selected from the group consisting of citrate ester, phthalate esters, esters with 1 to 16 carbon atoms (C1 to C16 esters) of α-hydroxy acids, oligomers of up to 10 units of α-hydroxy acids and, and C1 to C16 esters of these oligomers of α-hydroxy acids.

Embodiment [0026]

In some embodiments, such as but not limited to those described in embodiments [0001]-[0016], the optional removal of at least 60 weight % of the plasticizer from the processed polymer is executed, and at least 60 weight % of the plasticizer is removed prior to the packaging of the medical device formed from the processed polymer.

Embodiment [0027]

In some embodiments, such as but not limited to those described in embodiment [0026], at least 75 weight % of the plasticizer is removed prior to the packaging of the medical device.

Embodiment [0028]

In some embodiments, such as but not limited to those described in embodiment [0027], at least 80 weight % of the plasticizer is removed prior to the packaging of the medical device.

Embodiment [0029]

In some embodiments, such as but not limited to those described in embodiment [0028], at least 90 weight % of the plasticizer is removed prior to the packaging of the medical device.

Embodiment [0030]

In some embodiments, such as but not limited to those described in embodiment [0029], at least 95 weight % of the plasticizer is removed prior to the packaging of the medical device.

Embodiment [0031]

In some embodiments, such as but not limited to those described in embodiment [0030], at least 97 weight % of the plasticizer is removed prior to the packaging of the medical device.

Embodiment [0032]

In some embodiments, such as but not limited to those described in embodiment [0031], at least 98 weight % of the plasticizer is removed prior to the packaging of the medical device.

Embodiment [0033]

In some embodiments, such as but not limited to those described in embodiment [0032], at least 99 weight % of the plasticizer is removed prior to the packaging of the medical device.

Embodiment [0034]

In some embodiments, such as but not limited to those described in embodiment [0033], at least 99.5 weight % of the plasticizer is removed prior to the packaging of the medical device.

Embodiment [0035]

In some embodiments, such as but not limited to those described in embodiments [0026]-[0034], at least one additional processing operation is executed, the at least one additional processing operation comprising heating the polymer to a temperature between the glass transition temperature of the polymer or 28° C., if the glass transition temperature is lower than 25° C., and the melting temperature of the polymer, if the polymer has a melting temperature above 28° C., or, if the polymer does not have a melting temperature above 28° C., the temperature that is 75° C. greater than the glass transition temperature, or 60° C., whichever is higher; and the plasticizer is removed during, after, or both during and after the at least one additional processing operation is executed, the at least one additional processing operation comprising heating the polymer to a temperature as described above.

Embodiment [0036]

In some embodiments, such as but not limited to those described in embodiment [0035], the removal occurs after the at least one additional processing operation comprising the heating of the polymer.

Embodiment [0037]

In some embodiments, such as but not limited to those described in embodiment [0035], the removal occurs during the at least one additional processing operation comprising the heating of the polymer.

Embodiment [0038]

In some embodiments, such as but not limited to those described in embodiment [0035], the removal occurs both during and after the at least one additional processing operation comprising the heating of the polymer.

Embodiment [0039]

In some embodiments, such as but not limited to those described in embodiment [0035], the removal occurs both during and after the at least one additional processing operation comprising the heating of the polymer, and at least 60 weight % of the plasticizer is removed after the additional processing operation.

Embodiment [0040]

In some embodiments, such as but not limited to those described in embodiments [0035]-[0039], the melt processing operation comprises extrusion, injection molding, or a combination thereof to form a polymer tube, and the at least one additional processing operation comprising heating the polymer tube to a temperature between the glass transition temperature of the polymer or 28° C., if the glass transition temperature is lower than 25° C., and the melting temperature of the polymer, if the polymer has a melting temperature above 28° C., or, if the polymer does not have a melting temperature above 28° C., the temperature that is 75° C. greater than the glass transition temperature, or 60° C., whichever is higher.

Embodiment [0041]

In some embodiments, such as but not limited to those described in embodiment [0040], the at least one additional processing operation comprising the heating of the polymer tube comprises axial extension of the polymer tube, radial expansion of the polymer tube, or a combination of radial expansion and axial extension of the polymer tube.

Embodiment [0042]

In some embodiments, such as but not limited to those described in embodiment [0041], the polymer tube is radially expanded and axially extended sequentially.

Embodiment [0043]

In some embodiments, such as but not limited to those described in embodiment [0041], the polymer tube is radially expanded and axially extended at least partially concurrently.

Embodiment [0044]

In some embodiments, such as but not limited to those described in embodiments [0041]-[0043], after the expansion, the tube wall thickness is at least 5 microns, but not more than 250 microns.

Embodiment [0045]

In some embodiments, such as but not limited to those described in embodiments [0041]-[0043], after the expansion, the tube wall thickness is in the range of about 70 to about 200 microns.

Embodiment [0046]

In some embodiments, such as but not limited to those described in embodiments [0040]-[0045], the method additionally comprises forming a pattern in the polymer tube to form the medical device.

Embodiment [0047]

In some embodiments, such as but not limited to those described in embodiment [0046], forming a pattern comprising laser cutting.

Embodiment [0048]

In some embodiments, such as but not limited to those described in embodiments [0026]-[0047], the removal of the plasticizer comprises heating the polymer to a temperature greater than the glass transition temperature of the polymer or 28° C., if the glass transition temperature is lower than 25° C., and less than the melting temperature of the polymer, if the polymer has a melting temperature above 28° C., or if the polymer does not have a melting temperature above 28° C., the temperature that is 75° C. greater than the glass transition temperature, or 60° C., whichever is higher.

Embodiment [0049]

In some embodiments, such as but not limited to those described in embodiment [0048], the heating occurs at a pressure below 200 Torr.

Embodiment [0050]

In some embodiments, such as but not limited to those described in embodiments [0048] and [0049], the heating occurs in an environment with a humidity of at least 25% relative humidity (rh) and not more than 100% rh.

Embodiment [0051]

In some embodiments, such as but not limited to those described in embodiment [0050], the heating occurs in an environment with a humidity of at least 40% rh and not more than 100% rh.

Embodiment [0052]

In some embodiments, such as but not limited to those described in embodiment [0050], the heating occurs in an environment with a humidity of at least 60% rh and not more than 100% rh.

Embodiment [0053]

In some embodiments, such as but not limited to those described in embodiment [0050], the heating occurs in an environment with a humidity of at least 80% rh and not more than 100% rh.

Embodiment [0054]

In some embodiments, such as but not limited to those described in embodiment [0048] and [0049], during the heating, the polymer is exposed to solvent vapor, and the solvent is a good solvent for the plasticizer.

Embodiment [0055]

In some embodiments, such as but not limited to those described in embodiment [0054], the solvent at least partially plasticizes the polymer.

Embodiment [0056]

In some embodiments, such as but not limited to those described in embodiments [0054] and [0055], the partial pressure of the solvent vapor is at least 20 Torr.

Embodiment [0057]

In some embodiments, such as but not limited to those described in embodiment [0056], for a duration of at least 2 minutes, the polymer is exposed to solvent vapor at a partial pressure of the solvent vapor of at least 20 Torr.

Embodiment [0058]

In some embodiments, such as but not limited to those described in embodiments [0054]-[0057], after the heating of the polymer in the presence of solvent vapor is complete, the polymer is heated for a duration of time of not less than 10 minutes to a temperature greater than the glass transition temperature of the polymer or 28° C., if the glass transition temperature is lower than 25° C., and less than the melting temperature of the polymer, if the polymer has a melting temperature above 28° C., or, if the polymer does not have a melting temperature above 28° C., a temperature that is 75° C. greater than the glass transition temperature, or 60° C., whichever is higher, without solvent vapor present, or with less than 1000 ppm solvent vapor present.

Embodiment [0059]

In some embodiments, such as but not limited to those described in embodiment [0058], at least 90 weight % of the solvent that is absorbed into the polymer during the removal of the plasticizer is removed before the medical device is packaged.

Embodiment [0060]

In some embodiments, such as but not limited to those described in embodiments [0001]-[0059], the medical device is an implantable medical device, a device used to support a surgical procedure, an extravascular wrap, a stent, an implantable drug delivery device, a peripheral stent, a coronary stent, a urethral stent, a bile duct stent, a tear duct stent, an intrapulmonary stent, or a tracheal stent.

Embodiment [0061]

A method of fabricating a medical device, the method including, but not limited to: forming a polymer construct comprising a polymer and optionally another material using a solvent based process; forming a medical device from the polymer construct where the forming comprises executing at least one processing operation comprising heating the polymer construct to a temperature between the glass transition temperature of the polymer, or 28° C., if the glass transition temperature is lower than 25° C., and the melting temperature of the polymer, if the polymer has a melting temperature above 28° C., or, if the polymer does not have a melting temperature above 28° C., the temperature that is 75° C. greater than the glass transition temperature, or 60° C., whichever is higher; and at the initiation of the at least one processing operation, the residual solvent in the polymer construct is not less than 0.1% by weight, and not more than 20% by weight. With respect to this method, the glass transition temperature refers to the glass transition temperature as plasticized by the residual solvent present in the polymer at the time.

Embodiment [0062]

In some embodiments, such as but not limited to that described in embodiment [0061], at the initiation of the at least one processing operation, the residual solvent in the polymer construct is not less than 0.2% by weight, and not more than 15% by weight.

Embodiment [0063]

In some embodiments, such as but not limited to that described in embodiment [0061], at the initiation of the at least one processing operation, the residual solvent in the polymer construct is not less than 0.3% by weight, and not more than 10% by weight.

Embodiment [0064]

In some embodiments, such as but not limited to that described in embodiment [0061], at the initiation of the at least one processing operation, the residual solvent in the polymer construct is not less than 0.5% by weight, and not more than 12% by weight.

Embodiment [0065]

In some embodiments, such as but not limited to that described in embodiment [0061], at the initiation of the at least one processing operation, the residual solvent in the polymer construct is not less than 1%, but not more than 15% by weight.

Embodiment [0066]

In some embodiments, such as but not limited to that described in embodiment [0061], at the initiation of the at least one processing operation, the residual solvent in the polymer construct is not less than 2%, but not more than 15% by weight.

Embodiment [0067]

In some embodiments, such as but not limited to that described in embodiment [0061], at the initiation of the at least one processing operation, the residual solvent in the polymer construct is not less than 3%, but not more than 15% by weight.

Embodiment [0068]

In some embodiments, such as but not limited to that described in embodiment [0061], at the initiation of the at least one processing operation, the residual solvent in the polymer construct is not less than 4%, but not more than 15% by weight.

Embodiment [0069]

In some embodiments, such as but not limited to that described in embodiment [0061], at the initiation of the at least one processing operation, the residual solvent in the polymer construct is not less than 5%, but not more than 15% by weight.

Embodiment [0070]

In some embodiments, such as but not limited to those described in embodiments [0061]-[0069], the residual solvent level is not more than 1000 ppm at the initiation of the packaging of the medical device.

Embodiment [0071]

In some embodiments, such as but not limited to those described in embodiments [0061]-[0069], the residual solvent level is not more than 500 ppm at the initiation of the packaging of the medical device.

Embodiment [0072]

In some embodiments, such as but not limited to those described in embodiments [0061]-[0069], the residual solvent level is not more than 100 ppm at the initiation of the packaging of the medical device.

Embodiment [0073]

A method of fabricating a medical device, the method including, but not limited to including: forming a polymer construct comprising a polymer and optionally another material or providing a polymer construct comprising a polymer and optionally another material; exposing the polymer construct to solvent vapor for a sufficient time and at a sufficient level to plasticize the polymer such that the glass transition temperature of the polymer of the polymer construct is lowered by at least 5° C., by at least 10° C., by at least 15° C., or by at least 20° C., but not more than 75° C.; after the exposure, forming a medical device from the polymer construct, the forming comprising executing at least one operation comprising heating the polymer construct to a temperature between the glass transition temperature of the polymer as plasticized by the solvent, or 28° C., if the glass transition temperature as plasticized by the solvent is lower than 25° C., and the melting temperature of the polymer, if the polymer has a melting temperature above 28° C., or, if the polymer does not have a melting temperature, above 28° C., the temperature that is 75° C. greater than the glass transition temperature, or 60° C., whichever is higher.

Embodiment [0074]

In some embodiments, such as but not limited to those described in embodiments [0061]-[0073], the polymer construct is exposed to solvent vapor during the at least one operation comprising the heating of the polymer, and if the polymer construct comprises a solvent, the solvent of the exposure may be the same or different from the solvent in the polymer construct at the initiation of the operation comprising the heating of the polymer construct.

Embodiment [0075]

In some embodiments, such as but not limited to those described in embodiment [0074], the polymer construct is a tube.

Embodiment [0076]

In some embodiments, such as but not limited to that described in embodiment [0075], the operation comprising the heating of the polymer comprises axial extension of the polymer tube, radial expansion of the polymer tube, or a combination of radial expansion and axial extension of the polymer tube.

Embodiment [0077]

In some embodiments, such as but not limited to that described in embodiment [0076], the tube is radially expanded and axially extended sequentially.

Embodiment [0078]

In some embodiments, such as but not limited to that described in embodiment [0076], the tube is radially expanded and axially extended at least partially concurrently.

Embodiment [0079]

In some embodiments, such as but not limited to those described in embodiments [0075]-[0078], the method additionally comprises forming a pattern in the tube to form the medical device.

Embodiment [0080]

In some embodiments, such as but not limited to those described in embodiment [0076], forming a pattern comprising laser cutting.

Embodiment [0081]

In some embodiments, such as but not limited to those described in embodiments [0073]-[0080], at least 60 weight % of the solvent absorbed into the polymer construct is removed from the polymer construct prior to packaging a medical device formed from the polymer construct, and at least 40 weight % and not more than 100 weight % of the removal of the absorbed solvent occurring after the operation comprising heating the polymer tube to a temperature between the glass transition temperature of the polymer, or 28° C., if the glass transition temperature is lower than 25° C., and the melting temperature of the polymer, if the polymer has a melting temperature above 28° C., or, if the polymer does not have a melting temperature above 28° C., the temperature that is 75° C. greater than the glass transition temperature as plasticized by the solvent, or 60° C., whichever is higher.

Embodiment [0082]

In some embodiments, such as but not limited to those described in embodiment [0081], at least 70 weight % of the absorbed solvent is removed prior to the packaging of the medical device.

Embodiment [0083]

In some embodiments, such as but not limited to those described in embodiment [0081], at least 80 weight % of the absorbed solvent is removed prior to the packaging of the medical device.

Embodiment [0084]

In some embodiments, such as but not limited to those described in embodiment [0081], at least 90 weight % of the absorbed solvent is removed prior to the packaging of the medical device.

Embodiment [0085]

In some embodiments, such as but not limited to those described in embodiment [0081], at least 95 weight % of the absorbed solvent is removed prior to the packaging of the medical device.

Embodiment [0086]

In some embodiments, such as but not limited to those described in embodiment [0081], at least 97 weight % of the absorbed solvent is removed prior to the packaging of the medical device.

Embodiment [0087]

In some embodiments, such as but not limited to those described in embodiment [0081], at least 98 weight % of the absorbed solvent is removed prior to the packaging of the medical device.

Embodiment [0088]

In some embodiments, such as but not limited to those described in embodiment [0081], at least 99 weight % of the absorbed solvent is removed prior to the packaging of the medical device.

Embodiment [0089]

In some embodiments, such as but not limited to those described in embodiment [0081], at least 99.5 weight % of the absorbed solvent is removed prior to the packaging of the medical device.

Embodiment [0090]

In some embodiments, such as but not limited to those described in embodiments [0073]-[0089], the absorbed solvent level in the medical device made from the polymer construct is not more than 1000 ppm at the initiation of the packaging of the medical device.

Embodiment [0091]

In some embodiments, such as but not limited to those described in embodiments [0073]-[0089], the level of the absorbed solvent in the medical device made from the polymer construct is not more than 500 ppm at the initiation of the packaging of the medical device.

Embodiment [0092]

In some embodiments, such as but not limited to those described in embodiments [0073]-[0089], the level of the absorbed solvent in the medical device made from the polymer construct is not more than 100 ppm at the initiation of the packaging of the medical device.

Embodiment [0093]

In some embodiments, such as but not limited to those described in embodiments [0061]-[0092], optionally, one or more operations are executed to form the medical device from the polymer construct, and the medical device is packaged after the removal of at least 50 weight % of the absorbed solvent, if there is absorbed solvent, the removal of at least 50 weight % of the residual solvent, if there is residual solvent, or both, if there is absorbed solvent and residual solvent.

Embodiment [0094]

In some embodiments, such as but not limited to those described in embodiments [0061]-[0093], the medical device is an implantable medical device or a device used to support a surgical procedure.

Embodiment [0095]

In some embodiments, such as but not limited to those described in embodiments [0061]-[0093], the medical device is an implantable medical device selected from the group consisting of extravascular wraps, stents, and implantable drug delivery devices.

Embodiment [0096]

In some embodiments, such as but not limited to those described in embodiments [0061]-[0093], the medical device is a stent selected from the group consisting of peripheral stents, coronary stents, urethral stents, bile duct stents, tear duct stents, intrapulmonary stents, and tracheal stents.

Embodiment [0097]

In some embodiments, such as but not limited to those described in embodiments [0001]-[0096], the polymer is a polymer for which at least one or the constituent monomer is selected from the group consisting of D,L-lactide, D,D-lactide, L,L-lactide, meso-lactide, glycolide, ε-caprolactone, trimethylene carbonate, p-dioxanone, ɤ-valerolactone, ɤ-undecalactone, and β-methyl-δ-valerolactone (and including individual monomers derived from any of the above which are dimers, trimers, etc., and specifically including D-lactic acid, L-lactic acid, and glycolic acid) and including copolymers of two or more of the constituent monomers above.

Embodiment [0098]

In some embodiments, such as but not limited to those described in embodiments [0001]-[0096], the polymer is poly(L-lactide) (PLLA), a copolymer with constitutional units derived from L-lactic acid being at least 30 mol % (% of moles) expressed as a %) and not more than 98 mol %, a copolymer with constitutional units derived from L-lactic acid being at least 50 mol % and not more than 98 mol %, a copolymer with a constitutional units derived from L-lactic acid being at least 60 mol % and not more than 98 mol %, a copolymer with constitutional units derived from L-lactic acid being at least 70 mol % and not more than 98 mol %, a copolymer with constitutional units derived from L-lactic acid being at least 80 mol % and not more than 98 mol %, a copolymer with constitutional units derived from L-lactic acid being at least 85 mol % and not more than 98 mol %, poly(L-lactide-co-glycolide) with at least 60 mol % being constitutional units derived from L-lactic acid the remainder derived from glycolic acid, poly(D,L-lactide-co-L-lactide)

with at least 60 mol % being constitutional units derived from L-lactic acid the remainder derived from D-lactic acid, poly(L-lactide-co-caprolactone) with at least 60 mol % being constitutional units derived from L-lactic acid, a copolymer with at least 75 weight % being constitutional units derived from L-lactic acid, a copolymer with at least 80 weight % being constitutional units derived from L-lactic acid, a copolymer with at least 85 weight % being constitutional units derived from L-lactic acid, or a combination thereof.

Embodiment [0099]

In some embodiments, such as but not limited to those described in embodiments [0001]-[0096], the polymer is a polymer or copolymer with constitutional units derived from L-lactic acid, glycolic acid, or a combination thereof, and optionally other constitutional units, and the polymer has a glass transition temperature of at least 28° C.

Embodiment [0100]

In some embodiments, such as but not limited to those described in embodiments [0001]-[0096], the polymer is a polymer or copolymer with constitutional units derived from L-lactic acid, glycolic acid, or a combination thereof, and optionally other constitutional units, and the polymer has a glass transition temperature of at least 30° C.

Embodiment [0101]

In some embodiments, such as but not limited to those described in embodiments [0001]-[0096], the polymer is a polymer or copolymer with constitutional units derived from L-lactic acid, glycolic acid, or a combination thereof, and optionally other constitutional units, and the polymer has a glass transition temperature of at least 37° C.

Embodiment [0102]

In some embodiments, such as but not limited to those described in embodiments [0001]-[0096], the polymer is a polymer or copolymer with constitutional units derived from L-lactic acid, glycolic acid, or a combination thereof, and optionally other constitutional units, the polymer has a glass transition temperature of at least 37° C. when saturated with water at 37° C.

Embodiment [0103]

In some embodiments, such as but not limited to those described in embodiments [0001]-[0096], the or at least one constitutional unit is derived from a hydroxy acid.

Embodiment [0104]

In some embodiments, such as but not limited to those described in embodiments [0001]-[0096], the or at least one constitutional unit is derived from an alpha-hydroxy acid.

Embodiment [0105]

In some embodiments, such as but not limited to those described in embodiments [0001]-[0104], the polymer has a number average molecular weight greater than 250,000 g/mole, but not more than 3,000,000 g/mole, as determined by gel permeation chromatography using polystyrene standards.

Embodiment [0106]

In some embodiments, such as but not limited to those described in embodiments [0001]-[0104], the polymer has a number average molecular weight greater than 300,000 g/mole, but not more than 3,000,000 g/mole, as determined by gel permeation chromatography using polystyrene standards.

Embodiment [0107]

In some embodiments, such as but not limited to those described in embodiments [0001]-[0104], the polymer has a number average molecular weight greater than 350,000 g/mole, but not more than 3,000,000 g/mole, as determined by gel permeation chromatography using polystyrene standards.

Embodiment [0108]

In some embodiments, such as but not limited to those described in embodiments [0001]-[0104], the polymer has a number average molecular weight greater than 400,000 g/mole, but not more than 3,000,000 g/mole, as determined by gel permeation chromatography using polystyrene standards.

Embodiment [0109]

In some embodiments, such as but not limited to those described in embodiments [0001]-[0104], the polymer has a number average molecular weight greater than 500,000 g/mole, but not more than 3,000,000 g/mole, as determined by gel permeation chromatography using polystyrene standards.

Embodiment [0110]

In some embodiments, such as but not limited to those described in embodiments [0001]-[0104], the polymer has a number average molecular weight greater than 600,000 g/mole, but not more than 3,000,000 g/mole, as determined by gel permeation chromatography using polystyrene standards.

Embodiment [0111]

In some embodiments, such as but not limited to those described in embodiments [0001]-[0104], the polymer has a number average molecular weight greater than 750,000 g/mole, but not more than 3,000,000 g/mole, as determined by gel permeation chromatography using polystyrene standards.

Embodiment [0112]

In some embodiments, such as but not limited to those described in embodiments [0001]-[0104], the polymer has a weight average molecular weight greater than 300,000 g/mole, but not more than 4,500,000 g/mole.

Embodiment [0113]

In some embodiments, such as but not limited to those described in embodiments [0001]-[0104], the polymer has a weight average molecular weight greater than 350,000 g/mole, but not more than 4,500,000 g/mole.

Embodiment [0114]

In some embodiments, such as but not limited to those described in embodiments [0001]-[0104], the polymer has a weight average molecular weight greater than 400,000 g/mole, but not more than 4,500,000 g/mole.

Embodiment [0115]

In some embodiments, such as but not limited to those described in embodiments [0001]-[0104], the polymer has a weight average molecular weight greater than 450,000 g/mole, but not more than 4,500,000 g/mole.

Embodiment [0116]

In some embodiments, such as but not limited to those described in embodiments [0001]-[0104], the polymer has a weight average molecular weight greater than 500,000 g/mole, but not more than 4,500,000 g/mole.

Embodiment [0117]

In some embodiments, such as but not limited to those described in embodiments [0001]-[0104], the polymer has a weight average molecular weight greater than 675,000 g/mole, but not more than 4,500,000 g/mole.

Embodiment [0118]

In some embodiments, such as but not limited to those described in embodiments [0001]-[0104], the polymer has a weight average molecular weight greater than 800,000 g/mole, but not more than 4,500,000 g/mole.

Embodiment [0119]

In some embodiments, such as but not limited to those described in embodiments [0001]-[0104], the optional other material is present and is an absorbable metal, an absorbable glass, or a combination thereof.

Embodiment [0120]

In some embodiments, such as but not limited to those described in embodiments [0001]-[0119], the optional other material is present and is an absorbable metal.

Embodiment [0121]

In some embodiments, such as but not limited to those described in embodiments [0001]-[0119], the optional other material is present and is an absorbable glass.

Embodiment [0122]

In some embodiments, such as but not limited to those described in embodiments [0001]-[0119], the optional other material is present and is a combination of an absorbable metal and an absorbable glass.

Embodiment [0123]

In some embodiments, such as but not limited to those described in embodiments [0001]-[0119], the optional other material is present and is a drug.

Embodiment [0124]

In some embodiments, such as but not limited to those described in embodiments [0001]-[0119], the optional other material is present and is a drug in combination with an absorbable glass, an absorbable metal, or both.

In those embodiments of the present invention that refer to the glass transition temperature of a polymer, such as without limitation, those embodiments described in the above labeled embodiments [0001]-[0124] which refer to the glass transition temperature of a polymer, to the extent logically consistent, the embodiments of the present invention encompass using the lowest, highest, or any one of the one or more intermediate glass transition temperatures, if one or more intermediate glass transition temperature exists. Similarly, with respect to embodiments of the present invention that refer to the melting temperature of a polymer, such as without limitation, those embodiments described in the above labeled embodiments [0001]-[0124] which refer to the melting temperature of a polymer, to the extent logically consistent, embodiments of the present invention encompass using the lowest, highest, or any one of the one or more intermediate melting temperatures, if one or more intermediate melting temperature exists. One of skill in the art, based on the disclosure herein, will be able to determine the appropriate glass transition temperature, appropriate melting temperature, or both for use in the various embodiments of the present invention, and will be able to determine which glass transition temperature, melting temperature, or both, are logically consistent with the embodiments described herein.

BRIEF DESCRIPTION OF THE DRAWINGS

FIG. 1 depicts an exemplary stent.

DETAILED DESCRIPTION OF THE INVENTION

Use of the term "herein" encompasses the specification, the abstract, and the claims of the present application.

Use of the singular herein includes the plural and vice versa unless expressly stated to be otherwise. That is, "a" and "the" refer to one or more of whatever the word modifies. For example, "a drug" may refer to one drug, two drugs, etc. Likewise, "the stent" may refer to one, two or more stents, and "the polymer" may mean one polymer or a plurality of polymers. By the same token, words such as, without limitation, "stents" and "polymers" would refer to one stent or polymer as well as to a plurality of stents or polymers unless it is expressly stated that such is not intended.

As used herein, unless specifically defined otherwise, any words of approximation such as without limitation, "about," "essentially," "substantially," and the like mean that the element so modified need not be exactly what is described but can vary from the description. The extent to which the description may vary will depend on how great a change can be instituted and have one of ordinary skill in the art recognize the modified version as still having the properties, characteristics and capabilities of the unmodified word or phrase. With the preceding discussion in mind, a numerical value herein that is modified by a word of approximation may vary from the stated value by ±15% in some embodiments, by ±10% in some embodiments, by ±5% in some embodiments, or in some embodiments, may be within the 95% confidence interval. For example, the term "consisting essentially of" may be 85%-100% in some embodiments, may be 90%-100% in some embodiments, or may be 95%-100% in some embodiments.

As used herein, any ranges presented are inclusive of the end-points. For example, "a temperature between 10° C. and 30° C." or "a temperature from 10° C. to 30° C." includes 10° C. and 30° C., as well as any temperature in between. In addition, throughout this disclosure, various aspects of this invention may be presented in a range format. The description in range format is merely for convenience and brevity and should not be construed as an inflexible limitation on the scope of the invention. Accordingly, the description of a range should be considered to have specifically disclosed all the possible subranges as well as individual numerical values, both integers and fractions, within that range. As an example, a description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. Unless expressly indicated, or from the context clearly limited to integers, a description of a range such as from 1 to 6 should be considered to have specifically disclosed subranges 1.5 to 5.5, etc., and individual values such as 3.25, etc. This applies regardless of the breadth of the range.

A stent or scaffold is a type of medical device, specifically an implantable medical device. As used herein, an "implantable medical device" refers to any type of appliance that is totally or partly introduced, surgically or medically, into a patient's body or by medical intervention into a natural orifice, and which is intended to remain there after the procedure. The duration of implantation may be essentially permanent, i.e., intended to remain in place for the remaining lifespan of the patient; until the device biodegrades; or until it is physically removed. Examples of implantable medical devices include, without limitation, implantable cardiac pacemakers and defibrillators; leads and electrodes for the preceding; implantable organ stimulators such as nerve, bladder, sphincter and diaphragm stimulators, cochlear implants; prostheses, vascular grafts, self-expandable stents, balloon-expandable stents, stent-grafts, grafts, artificial heart valves, foramen *ovale* closure devices, cerebrospinal fluid shunts, orthopedic fixation devices, and intrauterine devices.

Other medical devices may be referred to as insertable medical devices that are any type of appliance that is totally or partly introduced, surgically or medically, into a patient's body or by medical intervention into a natural orifice, but the device does not remain in the patient's body after the procedure.

As noted above a stent is a type of implantable medical device. Stents are generally cylindrically shaped and function to hold open, and sometimes expand, a segment of a blood vessel or other vessel in a patient's body when the vessel is narrowed or closed due to diseases or disorders including, without limitation, tumors (in, for example, bile ducts, the esophagus, the trachea/bronchi, etc.), benign pancreatic disease, coronary artery disease, carotid artery disease and peripheral arterial disease. A stent can be used in, without limitation, the neuro, carotid, coronary, pulmonary, aorta, renal, biliary, iliac, femoral and popliteal, as well as other peripheral vasculatures, superficial femoral artery, and in other bodily lumens such as the urethra or bile duct. A stent can be used in the treatment or prevention of disorders such as, without limitation, atherosclerosis, vulnerable plaque, thrombosis, restenosis, hemorrhage, vascular dissection and perforation, vascular aneurysm, chronic total occlusion, claudication, anastomotic proliferation, bile duct obstruction and ureter obstruction.

Another type of medical device is a vascular catheter, which is a type of insertable device. A vascular catheter is a thin, flexible tube with a manipulating means at one end, referred to as the proximal end, which remains outside the patient's body, and an operative device at or near the other end, called the distal end, which is inserted into the patient's artery or vein. The catheter may be introduced into a patient's vasculature at a point remote from the target site, e.g., into the femoral artery of the leg where the target is in the vicinity of the heart. The catheter is steered, assisted by a guide wire than extends through a lumen, which is a passageway or cavity, in the flexible tube, to the target site whereupon the guide wire is withdrawn. After the guidewire is withdrawn, the lumen may be used for the introduction of fluids, often containing drugs, to the target site. For some vascular catheters there are multiple lumens allowing for the passage of fluids without removal of the guidewire. A catheter may also be used to deliver a stent or may be used to deliver a balloon used in angioplasty. Moreover, vascular catheters have a length to diameter ratio of at least 50/1.

As used herein, a "balloon" refers to the well-known in the art device, usually associated with a vascular catheter, that comprises a relatively thin, flexible material, forming a tubular membrane, that when positioned at a particular location in a patient's vessel may be expanded or inflated to an outside diameter that is essentially the same as the inside or luminal diameter of the vessel in which it is placed. In angioplasty procedures, the balloon is expanded to a size larger than the luminal diameter of the vessel, as it is a diseased state, and closer to the luminal size of a healthy reference section of vessel. In addition to diameter, a balloon has other dimensions suitable for the vessel in which it is to be expanded. Balloons may be inflated, without limitation, using a liquid medium such as water, aqueous contrast solution, or normal saline solution, that is, saline that is essentially isotonic with blood.

A "balloon catheter" refers to medical device which is a system of a catheter with a balloon at the end of the catheter.

A balloon, a catheter, and a stent differ. Stents are typically delivered to a treatment site by being compressed or crimped onto a catheter or onto a catheter balloon, and then delivered through narrow vessels to a treatment site where the stent is deployed. Deployment involves expanding the stent to a larger diameter, typically to the diameter of the vessel (or closer to the luminal size of a healthy reference section of vessel), once it is at the treatment site. Stents can be self-expanding or balloon expandable. The expanded stent is capable of supporting a bodily lumen for an extended period of time. In contrast, a balloon has a wall thickness that is so thin that the tubular membrane cannot support a load at a given diameter unless inflated with a fluid, such as a liquid or gas. Furthermore, a balloon is a transitory device that is inserted in the patient's body for only a limited time for the purpose of performing a specific procedure or function. Unlike a stent, dilatation balloons are not permanently implanted within the body.

The structure of a stent is typically a generally cylindrical or tubular form (but the precise shape may vary from the shape of a perfect cylinder), and the tube or hollow cylinder may be perforated with passages that are slots, ovoid, circular, similar shapes, or any combination thereof. The perforations extend over the length of the stent, rather than being concentrated in one region of the length. In some embodiments, the perforations form at least 10%, preferably at least 20%, more preferably at least 25%, and more preferably at least 30%, but not more than 99% of the exterior surface area of the tube. A stent may be composed of scaffolding that includes a pattern or network of interconnecting structural elements or struts. The scaffolding can be formed from tubes, or sheets of material, which may be perforated or unperforated, rolled into a cylindrical shape and welded or otherwise joined together to form a tube. A pattern may be formed in the tube by laser cutting, chemical etching, etc.

A non-limiting example of a stent 100 is depicted in FIG. 1. As noted above, a stent may be a scaffolding having a pattern or network of interconnecting structural elements or struts 105, which are designed to contact the walls of a vessel and to maintain vascular patency, that is to support the bodily lumen. Struts 105 of stent 100 include luminal faces or surfaces 110 (facing the lumen), abluminal faces or surfaces 115 (tissue facing), and side-wall faces or surfaces 120. The pattern of structural elements 105 can take on a variety of patterns, and the structural pattern of the device can be of virtually any design. Typical expanded diameters of a stent range from approximately 1.5 mm to 35 mm, preferably from approximately 2 mm to 10 mm, and for a coronary stent, from 1.5-6.0 mm. The length to diameter ratio of a stent is typically from 2 to 25. The embodiments disclosed herein are not limited to stents, or to the stent pattern, illustrated in FIG. 1.

Other types of stents or endoprotheses are those formed of wires, such as the Wallsten endoprosthesis, U.S. Pat. No. 4,655,771, and those described in U.S. Pat. No. 7,018,401 B1 and U.S. Pat. No. 8,414,635 B2. Those described in U.S. Pat. No. 7,018,401 B1 and U.S. Pat. No. 8,414,635 B include, but are not limited to, a plurality of shape memory wires woven together to form a body suitable for implantation into an anatomical structure. These devices may be of a substantially uniform diameter, or may have a variable diameter such as an hourglass shape. Other stent forms include helical coils.

The body, scaffolding, or substrate of a stent may be primarily responsible for providing mechanical support to walls of a bodily lumen once the stent is deployed therein. The "device body" of a medical device may be the functional device without a coating or layer of material different from that of which the device body is manufactured has been applied. If a device is a multi-layer structure, the device body may be the layer(s) that form the functional device, and for a stent this would be the layer(s) which support the bodily lumen. For a stent, the stent body may be the scaffolding, for example, as pictured in FIG. 1, without an exterior coating. If the body is manufactured by a coating process, the stent body can refer to a state prior to application of additional coating layers of different material, or application of layers not intended to form part of the structural support, which will be apparent to one of skill in the art. "Outer surface" of an implantable device, such as a stent, refers to any surface however spatially oriented that is in contact, or may be in contact, with bodily tissue or fluids. As a non-limiting example, for the stent shown in FIG. 1, the outer surface includes the abluminal surface, the luminal surface, and the sidewall surfaces.

Implantable and insertable medical devices can be made of virtually any material including metals and/or polymers including both bioabsorbable polymers, biostable polymers, and combinations thereof.

Although stents made of nonerodible metals and metal alloys have become the standard of care for treatment of artery disease, it is desirable to make stents out of biodegradable polymers. Obviously, a stent or other device formed of a biostable or durable material would remain in the body until removed. There are certain disadvantages to the presence of a permanent implant in a vessel such as compliance mismatch between the stent and vessel and risk of embolic events. The presence of a stent may affect healing of a diseased blood vessel. To alleviate such disadvantages, the stent can be made from materials that erode or disintegrate through exposure to conditions within the body. Thus, erodible portions of the stent can disappear from the implant region after the treatment is completed, leaving a healed vessel. Stents fabricated from biodegradable, bioabsorbable, and/or bioerodable materials such as bioabsorbable polymers can be designed to completely erode only after the clinical need for them has ended.

As noted above, the embodiments of the present invention encompass, but are not limited to, devices that are bioabsorbable and methods of forming such devices. As used herein, the terms "biodegradable," "bioabsorbable," "bioresorbable," and "bioerodable" are used interchangeably, and refer to materials, such as but not limited to, polymers, which are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes. Conversely, the term "biostable" refers to materials that are not biodegradable, or biodegrade over a very long time period, such as several decades.

The stent must be able to satisfy several mechanical requirements. The stent must have radial strength and sufficient strength and rigidity to support the walls of a vessel and withstand radially compressive forces. Longitudinal flexibility is required for delivery and deployment. Relatively high toughness or resistance to fracture is required for the material of the stent must be able to withstand crimping onto a delivery element, such as the balloon of a vascular catheter, as well as expansion when deployed. It must maintain its shape once deployed. For stents used in the superficial femoral artery (SFA), the mechanical requirements can be higher than for stents in coronary arteries as the SFA is subjected to various forces, such as compression, torsion, flexion, extension, and contraction, which place a high demand on the mechanical performance of implants. The mechanical requirements on a stent differ from those of other implantable medical devices such as catheters, which are not crimped to a smaller size and/or expanded.

Although biodegradable polymers can de designed to erode away, one drawback of polymers as compared to metals and metal alloys is that the strength to weight ratio of polymers is usually smaller than that of metals. To compensate for this, a polymeric stent can require significantly thicker struts than a metallic stent, which results in an un-desirably large profile. For example, a typical thickness for a strut in a metal stent is about 0.003".

To avoid large struts, polymers may be processed to improve strength and toughness. The use of polymers of higher molecular weights may also contribute to strength and toughness of the stent. The use of high molecular weight polymers may be used instead of or in addition to processing operations to increase polymer strength.

An example of some of the process operations that may be involved in fabricating a polymeric stent include, but are not limited to, the following:

(1) forming a polymeric tube using extrusion or injection molding, or by rolling and welding a polymer sheet which may be formed by extrusion, injection molding, solvent casting or another process;

(2) optionally radially deforming, axially deforming, or both (expanding, extending, or both expanding and extending) the formed tube by application of heat, pressure, or both;

(3) forming a stent from the deformed tube by cutting a stent pattern in the tube, which may be deformed, such as with chemical etching or laser cutting;

(4) optionally coating the stent with a coating including a drug;

(5) crimping the stent on a support element, such as a balloon on a delivery catheter;

(6) packaging the crimped stent/catheter assembly; and (7) sterilizing the stent assembly.

A noted in step (2), an extruded polymer tube may also be radially expanded, axially extended, or both radially expanded and axially extended. The tube may be radially expanded to increase its radial strength, which can also increase the radial strength of the stent. The radial expansion process tends to preferentially align the polymer chains along the radial or hoop direction which is believed result in enhanced radial strength. The radial expansion step assists in making a stent scaffolding with thin struts that is sufficiently strong to support a lumen upon implantation. The tube at both the initial and expanded diameter have wall thicknesses that are large enough that they can support an outward radial force or load. The radial expansion and axial extension may occur sequentially with either the radial expansion and the axial extension occurring first in time, and there may be a 15 second to 3 hour delay between the two operations. The radial expansion and axial extension may occur concurrently, where at least 50% of time, at least 70% of the time, or at least 90% of the time that the tube is being expanded, the tube is also being extended, or vice versa.

During the expansion step, the tube may be heated to a temperature between glass transition temperature ($T_g$) (provided the glass transition temperature is above about 25° C.), and the melting point of the polymer, if the polymer exhibits a melting point, and a higher temperature such as 20° C., 35° C., or 50° C. above the glass transition temperature of the polymer, if the polymer has no melting temperature, and the tube may be expanded to an expanded diameter. After expansion, the tube may be cooled to below the $T_g$ of the polymer, typically to ambient temperature (20° C. to 30° C.), to maintain the tube at an expanded diameter. The percent radial expansion may be between about 50% and 600%, preferably 300% to 500%, or any specific value within either of these ranges, such as about 400%. The percent radial expansion is defined as RE %=(RE ratio−1)×100%, where the RE Ratio=(Inside Diameter of Expanded Tube)/(Original Inside Diameter of the Tube). The percent axial extension expansion may be between about 10% and about 200%, preferably between about 15% and about 120%, or any specific value within either of these ranges, such as about 20%. The percent of axial extension that the polymer tube undergoes is defined as AE %=(AE ratio−1)×100%, where the AE Ratio=(Length of Extended Tube)/(Original Length of the Tube). The expansion of the tube decreases the wall thickness from about 300 to 600 microns (micrometers, $10^{-6}$ meters) to something in the range of about 70 to about 200 microns. The width and thickness of the struts of the stent can be, for example, between 90-160 microns.

After cutting a stent pattern into the tube, which may be deformed as noted in step (2), the stent scaffolding may then be optionally coated with a coating which may include a polymer and a drug. The drugs may be distributed uniformly or non-uniformly in a coating that is disposed over all of, substantially all of, or at least a portion of, the outer surface of the stent scaffolding.

In order to make the stent ready for delivery, the stent may be secured to a delivery element such as a delivery balloon. In this process, the stent is compressed to a reduced diameter or crimped over the balloon. During crimping and in the crimped state, some sections of the stent are subjected to high, localized stress and strain. Due to the fact that some regions of the stent structure are subjected to high compressive stress and strain, the stent during crimping and in the crimped state may be susceptible to cracking.

The stent is deployed by expanding it to an increased diameter at an implant site in a vessel which can be greater than the as-cut diameter of the stent. The deployed stent must have sufficient radial strength to apply an outward radial force to support the vessel at an increased diameter for a period of time.

Some of the methods used to form a stent or methods of forming a polymer tube or a polymer construct from which a stent is formed involve processing at high temperatures, such as at and/or above the melting point of the polymer. In addition, methods such as extrusion subject the polymer to high shear stresses. The exposure to high shear, to high temperatures, or both, may result in degradation of the polymer. The degradation may reduce the molecular weight of the polymer, and thus, potentially reduce the strength of the polymer. For higher molecular weight polymers, higher temperatures are needed to obtain a viscosity sufficiently low for processing.

As used herein, "polymer construct" refers to any useful article of manufacture made of a polymer. A polymer construct may be further processed to form a medical device. Some examples of polymer constructs include, but are not limited to, a tube, a sheet, a fiber, etc.

Various embodiments of the present invention encompass methods of forming a medical device, such as a stent, having a device body or scaffolding formed or fabricated from a polymer, and particularly, a bioabsorbable polymer. The various embodiments of the present invention encompass methods of using plasticizers and other materials to allow for processing of the polymer at lower temperatures, and with lower exposure to shear stress.

Although the discussion that follows may make reference to a stent or stents as the medical device, the embodiments of the present invention are not so limited, and encompass any medical device which may benefit from the embodiments of the invention. Examples of the other types of medical devices which may benefit from the embodiments of the present invention, include, without limitation, extravascular wraps, intrapulmonary or intra-urethral stents, stents for other than vascular lumens, drug delivery devices including implantable drug delivery devices, and any substrate that may be used to support a surgical procedure, such as and without limitation, a device used to support an anastomotic site via minimally invasive bypass surgery.

As used herein, "polymeric stent" refers to a stent having a scaffolding (or body) that is made completely, or substantially completely, from a polymer, or the scaffolding is made from a composition including a polymer and a material. If the scaffolding is made from a composition including a polymer and a material, the polymer is a continuous phase of the scaffolding, the scaffolding is at least 50% by weight polymer, or the scaffolding is at least 50% by volume polymer. In some embodiments, a polymeric stent may have a scaffolding made from a composition including a polymer and a material that is at least 70%, at least 80%, at least 90%, or at least 95% by volume or by weight polymer, but not more than 99.5% by volume or by weight polymer. Analogous definitions apply to a polymeric tube, a polymer construct, or a polymeric medical device except that the reference to the scaffolding would be replaced by "tube" for a polymer tube, "construct" for a polymer construct, and "device body" for a medical device.

Examples of semicrystalline polymers that may be used as the polymer in embodiments of the present invention include, without limitation, poly(L-lactide) (PLLA), polyglycolide (PGA), polymandelide (PM), polycaprolactone (PCL), poly(trimethylene carbonate) (PTMC), polydioxanone (PDO), poly(4-hydroxy butyrate) (MB), and poly(butylene succinate) (PBS). A non-limiting exemplary amorphous polymer that may be used as the polymer in the embodiments of the present invention is poly(D,L-lactide) (PDLLA). Additionally, block, random, and alternating copolymers of the above polymers may also be used in embodiments of the present invention, for example, poly(L-lactide-co-glycolide). The polymers described herein may be used individually, or in combination, in the embodiments of the present invention.

Embodiments encompass methods in which a plasticizer is blended with the polymer resin prior to, during, or both prior to and during a polymer processing operation in which the polymer is heated to a temperature above the melting temperature, or alternatively, if the polymer does not have a melting temperature, a temperature that is equal to or greater than 20° C., 35° C., 50° C., 75° C., or 100° C. above the glass transition temperature of the polymer ("melt processing operation"). Examples of such processing operations include, without limitation, extrusion which includes ram extrusion and use of an extruder such as a single screw extruder, twin screw extruder, pultrusion, injection molding, and compression molding.

In the various embodiments of the present invention the plasticizer used is a compound that is biocompatible and that has a boiling point greater than the highest temperature that will be encountered in the melt processing operation. In addition, the plasticizer may have some compatibility or miscibility with the polymer (such as at least 1 weight % solubility). The polymer may have an inherent viscosity of at least 3.3 dl/g, but not more than 15 dl/g. In some embodiments, the plasticizer may have a boiling point that is at least 3° C., at least 5° C., at least 10° C., or at least 15° C. higher than the highest temperature that will be encountered in by the polymer in the polymer processing operation described above. The plasticizers disclosed herein may be used individually or in combination. Some non-limiting examples include N-methyl pyrrolidone which has a boiling point (b.p.) of 203° C., isophorone with a b.p. of 215° C., butyl benzoate with a b.p. of 249° C., ethyl benzoate with a b.p. of 212° C., and sulfolane, with a b.p. of 285° C. In some embodiment, the methods use a plasticizer which specifically excludes any one or more members of the group consisting of acetone, 2-butanone, trichloroethylene, 1,1,1-trichloroethane, chloroform, dimethylacetamide, tetrahydrofuran, dioxanone, and cyclohexanone. In some embodiments, the plasticizer added is different from any solvent used in production of the polymer, and different from any solvent used in post-production processing of the polymer. In some embodiments, the plasticizer excludes water.

In some embodiments, at least 50% by weight of the plasticizer added remains in the stent and is part of the final packaged stent. In some embodiments, at least 75% by weight of the plasticizer, or at least 90% by weight of the plasticizer remains in the stent and is part of the final packaged stent. Examples of plasticizers that may remain in the stent include, without limitation, a constituent monomer of the polymer, or an oligomer thereof, and specifically an oligomer of 2 to 16 constitutional units, preferably 4 to 16 constitutional units. As an example, poly(L-lactide), may be plasticized by using the lactic acid monomer, or preferably, an oligomer such as L-lactide, the lactic acid dimer (or cyclic di-ester), or an oligomer of L-lactic acid with a least 3 lactic acid units, such as a trimer (3 lactic acid units) or tetramer (4 lactic acid units). Other examples of plasticizers that may be used in the embodiments of the present invention include, without limitation, citrate ester (Citroflex™), and phthalate esters. Non-limiting examples esters of phthalic acid include dimethyl phthalate, diethyl phthalate, diallyl phthalate, di-n-propyl phthalate, di-n-butyl phthalate, di-iso-butyl phthalate, butyl cyclohexyl phthalate, di-n-pentyl phthalate, dicyclohexyl phthalate, butyl benzyl phthalate, di-n-hexyl phthalate, di-iso-hexyl phthalate, di-iso-heptyl phthalate, butyl decyl phthalate, di(2-ethylhexyl) phthalate, di(n-octyl) phthalate, di-iso-octyl phthalate, n-octyl n-decyl phthalate, di-iso-nonyl phthalate, di(2-propylheptyl) phthalate, di-iso-decyl phthalate, diundecyl phthalate, di-iso-undecyl phthalate, ditridecyl phthalate, and di-isotridecyl phthalate. Other examples of plasticizers that may be used in the embodiments of the present invention include, without limitation, esters of hydroxy acids, including di-ester of hydroxy acids, or esters of oligomers of hydroxy acids, where the oligomer is of 2 to 16 constitutional units, and in some embodiments, 3 to 16 or 4 to 16 constitutional units. Esters include all hydrocarbon esters of 1 to 16 carbon atoms, whether linear, branched, cyclic or aromatic, of hydroxy acids. Preferred are plasticizers which are esters of the or a constituent monomer or esters of an oligomer of the or a constituent monomer of the polymer. As a non-limiting example, if the polymer is poly(L-lactide), then the additive may be an ester of lactic acid, lactide, or an oligomer of 3 or more constitutional units. Some non-limiting examples include ethyl lactate, butyl lactate, and lauryl lactate.

The plasticizer may be added in an amount in the range of 1 part by weight plasticizer to 5000 parts by weight polymer, to 1 part by weight plasticizer to 9 parts by weight polymer, preferably 1 part by weight plasticizer to 2000 parts by weight polymer, to 1 part by weight plasticizer to 15 parts by weight polymer, and more preferably, 1 part by weight plasticizer to 1000 parts by weight polymer, to 1 part by weight plasticizer to 20 parts by weight polymer. In some embodiments, the plasticizer added may be in the range of 1 part by weight plasticizer to 500 parts by weight polymer, to 1 part by weight plasticizer to 25 parts by weight polymer, or in the range of 1 part by weight plasticizer to 200 parts by weight polymer, to 1 part by weight plasticizer to 35 parts by weight polymer. In some embodiments, a sufficient amount of plasticizer is added to lower the glass transition temperature of the polymer by at least 5° C., by at least 10° C., by at least 15° C., or by at least 20° C., but not more than 75° C. In some embodiments, the amount of plasticizer that is added is the amount to lower the glass transition temperature by 5° C. to 50° C., or 10° C. to 40° C., which may be in the range of 2 to 25% by weight.

The drawback of the use of a plasticizer which remains in the polymer, and thus in the final packaged device, is that the glass transition temperature is lowered by the presence of the plasticizer. Although lowering of the glass transition temperature allows for melt processing at lower temperatures, the reduction of the glass transition of the polymer in the final product may reduce polymer strength. Thus, in some embodiments, the amount of plasticizer that is added is an amount to ensure that the glass transition temperature of the polymer is at least 37° C., at least 39° C., at least 40° C., at least 42° C., or at least 45° C. It may be especially preferred for the $T_g$ in the hydrated state of the polymer to be at least 37° C. Obviously, in these embodiments, the initial glass transition temperature of the polymer must be greater than 37° C. as the glass transition temperature is lowered by the addition of a plasticizer.

In some embodiments, the plasticizer is removed, or substantially removed, from the stent such that the final packaged stent is free of, or substantially free of, the added plasticizer. In some embodiments, at least 60 weight %, at least 75 weight %, at least 80 weight %, at least 90 weight %, at least 95 weight %, at least 97 weight %, at least 98 weight %, at least 99 weight %, or at least 99.5 weight % of the plasticizer that is added is removed from the stent prior to packaging. In some embodiments, the polymer of the stent body of the packaged stent includes not more than 50,000 ppm (parts per million by weight) of the added plasticizer, preferably not more than 20,000 ppm, more preferably not more than 10,000 ppm, and even more preferably, not more than 5000 ppm. In some embodiments, ideally, all plasticizer would be removed, but realistically a small amount may remain (such as and without limitation, around 0.005 ppm, and in some cases, higher).

The plasticizer may be removed after the melt processing operation and before the stent is packaged. In some embodiments, at least 60 weight %, at least 80 weight %, at least 90 weight %, at least 95 weight %, at least 97 weight %, at least 98 weight %, at least 99 weight %, or at least 99.5 weight % of the plasticizer that is added is removed after the melt processing operation and prior to the execution of any additional processing operations.

The plasticizer may be removed during, after, or both during and after an additional processing operation in which the polymer is heated to and maintained at a temperature between the glass transition temperature and an upper temperature. As used herein, the term "an upper temperature" when used in the context of the phrase "the glass transition temperature and an upper temperature" refers to the melting temperature, if the polymer exhibits one or more melting temperatures and at least one melting temperature is above 28° C., or alternatively, if the polymer does not have a melting temperature, a temperature that is not greater than 20° C., 35° C., or 50° C. above the glass transition temperature of the polymer, or 45° C. if the melting temperature is below 45° C. and 50° C. above the glass transition temperature of the polymer is below 45° C. In some embodiments, the additional processing operation may expose the polymer to a temperature that is greater than the glass transition temperature of the polymer, but less than the highest temperature of the polymer in the melt processing operation. The temperature may fluctuate or vary during the subsequent processing operation. Non-limiting examples of such subsequent operations include annealing, axial extension, radial expansion, or a combination of radial expansion and axial extension, where the annealing may be executed with one or more dimensions remaining constant, such as at constant diameter, constant length, or both.

In some embodiments, at least 50 weight %, at least 70 weight %, at least 85 weight %, at least 90 weight %, at least 95 weight %, at least 97 weight %, at least 98 weight %, at least 99 weight %, or at least 99.5 weight % of the added plasticizer is present at the initiation of the first or the only processing operation executed after the melt processing operation. In some of these embodiments, at least 60 weight %, at least 80 weight %, at least 90 weight %, at least 95 weight %, at least 97 weight %, at least 98 weight %, at least 99 weight %, or at least 99.5 weight % of the added plasticizer is removed prior to the completion of the processing operation subsequent to the completion of a melt processing operation.

In some embodiments, most of the plasticizer is removed after the first or the only processing operation after the melt processing operation. In those embodiments in which a subsequent processing operation will be executed in which the polymer is heated to a temperature above its glass transition temperature (provided the glass transition temperature is greater than 25° C.), it is preferably that not more than 20 weight %, not more than 15 weight %, or not more than 10 weight % of the plasticizer is removed after the melting operation and prior to the subsequent processing operation. In some embodiments, after the execution of the subsequent processing operation, the polymer may include 40 weight %, 60 weight %, 75 weight %, 85 weight % or 90 weight % of the added plasticizer. The presence of the plasticizer in the polymer during a subsequent processing operation may allow for processing at a lower temperature, with a reduced exposure to shear stress, or both, or otherwise enhance processing in the subsequent operation. As a non-limiting example, for a tube subject to radial expansion, axial extension, or both, the presence of a plasticizer may increase the rate of crystallization and impacts the orientation ratio (the fraction of crystallinity in the axial vs. the circumferential direction). In addition, for radial expansion of a polymer tube, the thickness decreases resulting in a shorter time for diffusion of the plasticizer from the polymer when removal of the plasticizer occurs after the execution of the expansion. As an example, the thickness of a polymer tube after radial expansion (optionally in combination with axial extension), may be 50% to 8% of the thickness of a polymer tube prior to expansion. The remaining plasticizer may be removed (or at least 90 weight %, at least 95 weight %, or at least 98 weight % of the remaining plasticizer) after the execution of the subsequent processing operation, but prior to additional processing operations, if any are executed, and packaging. In some embodiments, at least 50 weight % and not more than 90 weight % of the remaining plasticizer is removed during, after, or both during and after the subsequent operation, but before additional processing operations executed before packaging, such as and without limitation drug coating.

The various embodiments of the present invention encompass methods of removing the plasticizer from the polymer prior to packaging the stent. In some embodiments, the removal comprises heating the polymer to and maintaining the temperature at a temperature between the glass transition temperature and an upper temperature ("heating and maintaining operation"). The heating and maintaining operation may be a separate operation from the radial expansion, axial expansion, or both, even if the temperature is the same (or within ±5° C.) or within the same range (between the glass transition temperature and an upper temperature). Thus, the heating and maintaining operation is executed in addition to, and after the completion of, the subsequent processing operation in which the polymer is heated to a temperature between the glass transition temperature (provided the glass transition temperature is greater than 25° C.) and an upper temperature. In some embodiments, if the polymer has a glass transition temperature is greater than 25° C., the temperature of the heating and maintaining operation is between the glass transition temperature and 10° C. below the melting temperature, if the polymer has a melting temperature, or between 15° C. above the glass transition temperature and 15° C. below the melting temperature, if the polymer has a melting temperature and there is more than 30° C. between the glass transition temperature and the melting temperature. If the polymer has no melting temperature, the temperature of the heating and maintaining temperature may be between 5° C. and 45° C. above the glass transition temperature, or between 10° C. and 40° C. above the glass transition temperature. The temperature of the heating and maintaining operation may fluctuate. In any of the embodiments of the present invention, the polymer may have a glass transition temperature of at least 28° C., preferably at least 30° C., and in some embodiments, at least 37° C., or at least 37° C. when saturated with water at 37° C.

In some embodiments, the subsequent processing operation is an annealing operation in which the polymer is heated to and maintained at a temperature between the glass transition temperature and an upper temperature. Annealing processes are typically performed to allow for polymer relaxation, removal of residual stress from processing, or both. In some embodiments, the plasticizer is removed during the annealing process, that is at least 80 weight %, at least 85 weight %, at least 90 weight %, at least 98 weight % or at least 99 weight %, and up to 99.9999 weight % of the remaining added plasticizer is removed. In some embodiments, the duration of the annealing process is extended beyond the time frame for polymer relaxation, etc. to allow for plasticizer removal. In some embodiments, the duration is 1.2 times, 1.5 times, 2 times, or 3 times, and in some embodiments, greater than 3 times, longer than would have been required for only annealing.

In some embodiments, the heating and maintaining operation may be performed in a convection oven. In some embodiments, the polymer is in the form of a tube, and there is a flow of an air or another fluid, such as air or nitrogen, through the tube during the heating and maintaining operation. The flow may be such that the fluid has a velocity of 0.1 to 100 m/sec. The fluid entering the tube and before contacting the tube would be free of, or substantially free of (not more than 2500 ppm by weight or by volume) the plasticizer. A fluid may be a gas, a liquid, or a supercritical fluid.

In some embodiments, the heating and maintaining operation is executed in a vacuum, that is at a pressure below normal atmospheric pressure (760 Torr). In some embodiments, the pressure may be at least 0.001 Torr, and not more than 400 Torr, not more than 300 Torr, not more than 200 Torr, or more than 100 Torr, or not more than 50 Torr. The pressure may fluctuate. The operation may be executed in a vacuum oven.

In some embodiments, the heating and maintaining is executed in an atmosphere with water vapor present, that is in a high humidity environment. The high humidity environment may be a relative humidity between 40% and 99%, preferably between 60% and 97%, and more preferably between 80% and 95%. The high humidity environment may be at normal atmospheric pressure or in a vacuum (for example, <200 Torr) as discussed above. In some embodiments, there may be a container of water present in the environment of the polymer during the heating and maintaining operation to absorb the plasticizer. Alternatively or additionally, there may be a stream or flow of water near the polymer or in the environment of the polymer to absorb the plasticizer. The presence of water in a container, a flow of water, or both, may be in addition to, or instead of, the high humidity environment. The use of the high humidity environment, the presence of water, or both, are especially useful for water soluble plasticizers such as, without limitation, n-methyl pyrrolidone and sulfolane. Water may plasticize the polymer, allowing for easier removal of the plasticizer. As a non-limiting example, poly(L-lactide) absorbs up to about 0.75 weight % water, and water acts as a plasticizer.

After at least a portion of the plasticizer has been removed, the absorbed water may be removed (at least to the specification limits for the polymer, such as but not limited to 0.1 weight %) by another heating and maintaining operation where the stent is placed in an environment of low humidity (less than 40% rh, preferably lower than 30% rh, and more preferably lower than 20% rh, and at least 0.01% rh), or at least in which the humidity level is lower than the humidity of the high humidity environment. The duration of time of the operation in a low humidity environment may be different that the duration of the operation in a high humidity environment. In some embodiments, the water is removed by directing a flow of a fluid (in other words, blowing), such as dry nitrogen (less than 2500 ppm water by volume, or by weight), over, around, inside, through, adjacent to, or a combination thereof, the polymer. For example, if the polymer is a tube, air or another gas, may be blown through, around, or both through and around the tube.

In some embodiments, the heating and maintaining may be executed in an environment of solvent vapor, where the solvent is not water, but may be a blend of water and another solvent. As used herein, with reference to placing a polymer in an atmosphere of a solvent vapor, a solvent will refer to a substance, including a fluid, that plasticizes, swells, or both plasticizes and swells the polymer. Solvents may be used individually or in combination. The plasticization, swelling, or both, of the polymer allows for easier removal of the plasticizer. In some embodiments, the solvent partial pressure is between 1 Torr and 200 Torr. In some embodiments, the solvent partial pressure is greater than 200 Torr. In some embodiments, the solvent partial pressure is at least 25%, preferably at least 50%, and more preferably at least 75% of the vapor pressure of the solvent at the temperature of treatment, and may be up to the vapor pressure of the solvent at the temperature of the operation. In some embodiments, the solvent is above its boiling point. Preferred solvents are those of a relatively low boiling point at atmospheric pressure, that is less than or equal to 80° C., and in some embodiments, less than or equal to 60° C. Some non-limiting examples of solvents that may be useful for the poly(L-lactide), or a copolymer with a constitutional unit derived from L-lactic acid, include methanol, ethanol, n-propanol, isopropanol, butanol, fluoroform, freons, methylene chloride ($CH_2Cl_2$), chloroform ($CHCl_3$), dimethyl ether, and ethylene oxide. FREON® is the trade name of DuPont for a number of chlorofluorocarbons, chlorofluorohydrocarbons, fluoro-hydrocarbons, and halons. Halons are hydrocarbons in which one or more hydrogen atoms are replaced with bromine, and other hydrogen atoms with other halogen atoms (fluorine, chlorine, and iodine). FREON® solvents include, HFC134A™, the trade name for 1,1,1,2-tetrafluoroethane ($CF_3CFH_2$), and HFC-227Ea™, the trade name for 1,1,1,2,3,3,3-heptafluoropropane ($CF_3CHFCF_3$). HFC-134a has a boiling point of −26° C. HFC-227ea has a boiling point of −16° C. Ethylene oxide is also a sterilant. In some embodiments, the solvent vapor is of a solvent that may at least partially dissolve the plasticizer (at least 10 g/liter solubility).

The amount of solvent absorbed by the polymer may be in the range of 0.01 weight % to 20 weight %, preferably 0.02 weight % to 15 weight %, more preferably 0.1 weight % to 12 weight %, and even more preferably 0.2 weight % to 10 weight %. In some embodiments, the amount of solvent absorbed by the polymer may be in the range of 0.1% to 8 weight %, 2 weight % to 15 weight %, or 5 weight % to 30 weight %. In some embodiments, a sufficient amount of solvent is absorbed to lower the glass transition temperature of the polymer by at least 5° C., by at least 10° C., by at least 15° C., or by at least 20° C., but not more than 75° C. In some embodiments, the amount of solvent absorbed by the polymer, in the range of 0.1 weight % to 35 weight %, lowers the glass transition temperature by 5° C. to 50° C., or 10° C. to 40° C.

In some embodiments, the solvent vapor is from a solvent that is different from any solvent used in production of the polymer, and different from any solvent used in post-production processing of the polymer. In some embodiments, the solvent vapor is from a solvent that is different from a solvent used in the immediately preceding processing operation. In some embodiments, the solvent vapor is of a solvent different from any one or more members of the group of acetone, 2-butanone, trichloroethylene, 1,1,1-trichloroethane, chloroform, cyclohexanone, dimethylacetamide, tetrahydrofuran, and dioxane.

In some embodiments, there is at least 30 seconds, preferably at least 1 minute, and more preferably at least 2 minutes, between the previous operation of processing the polymer and the heating and maintaining operation with solvent vapor present. In some embodiments, there is at least 30 minutes between the previous operation of processing the polymer and the heating and maintaining operation with solvent vapor present.

After at least a portion of the plasticizer is removed, then the solvent may be removed from the polymer. The subsequent removal of the solvent may be accomplished by a subsequent heating and maintaining operation where no solvent vapor is added to the environment. In some embodiments, the polymer is moved to a new environment which is initially free of, or substantially free of (<2500 ppm by weight or volume) the solvent vapor. In some environments, there is a flow of a fluid such as air or nitrogen around, inside, over, or adjacent to the polymer, and the fluid that flows is initially (prior to contact with the polymer or as provided to the environment of the polymer) free of or substantially free of (<2500 ppm by weight or volume) the solvent vapor. However, as the operation is executed there will be solvent vapor present in the environment due to the evaporation or diffusion from the polymer. In some embodiments, a subsequent heating and maintaining operation is executed for removal of the solvent for a duration of time of not less than 10 minutes, and not more than 24 hours, with the solvent partial pressure in the environment that is less than 50%, and preferably, less than 25% of the vapor pressure of the pure solvent at the temperature of the operation, or less than 2500 ppm solvent vapor. In some embodiments, at least 90 weight %, at least 95 weight %, or at least 98 weight % of the solvent absorbed into the polymer during the operation is removed from the polymer. In some embodiments, the residual solvent in the polymer after solvent removal is not more than 1000 ppm (parts per million by weight), not more than 500 ppm, or not more than 100 ppm.

The duration of a heating and maintaining operation may range from 10 minutes to 240 hours or more, whether performed at normal atmospheric pressure, in a vacuum, in a high humidity environment, in the presence of a solvent vapor, or a combination thereof. If the heating and maintaining operation in the absence of a vacuum, a high humidity environment, or a solvent vapor, the duration may be longer than if the execution occurs in the presence of one or more of a vacuum, a high humidity environment, and a solvent vapor. In some embodiments, the duration is from 10 minutes to 2 hours, 30 minutes to 4 hours, 1 to 10 hours, 1 to 12 hours, 2 to 16 hours, 2 to 24 hours, 4 to 48 hours, 12 to 72 hours, or 24 to 200 hours.

In some embodiments, the polymer is not subject to a melt processing operation, but a polymer construct, such as a polymer tube or polymer sheet, may be formed using a solvent based method. Examples of such solvent based methods include, without limitation, solvent casting, dipping, spraying, ink-jet printing, direct application of a coating, gel extrusion, and ram extrusion. As used herein, a "solvent" when references is made to a solvent based method of production of a polymer construct is a substance, including a fluid, that can dissolve, partially dissolve, or disperse the polymer sufficiently to execute the processing operation. As an example, a solvent for a dipping process would likely be a substance that can dissolve the polymer, or at least sufficiently disperse the polymer. The advantage of solvent based methods are that the polymer is not exposed the temperatures or shear stress that would be encountered in a melt processing operation, such as extrusion. In many cases, the polymer may be processed at a temperature below the melting temperature, or in some cases, at a temperature below the polymer's unplasticized glass transition temperature (glass transition temperature without absorbed solvent). As a result, there is less polymer degradation, and in many cases, minimal polymer degradation (<5% change in the number average molecular weight). The polymer may have an inherent viscosity of at least 3.3 dl/g, but not more than 15 dl/g.

Most often the solvents used in the processing the polymer also plasticizes the polymer, and thus, residual solvent from the solvent processing operation may act as a plasticizer providing the advantages described above in subsequent processing operations. As a non-limiting example, for the polymer poly(L-lactide), processing may occur at a temperature in the range of 75° C. to 175° C. due to plasticization by residual solvent. Conventionally, polymerization is performed to result in a product with a monomer content as low as possible. Additionally, monomer extraction conventionally is applied to remove all monomer or as much as practically possible from a polymer. Typically, after a process utilizing a solvent is complete, residual solvent used in processing the polymer is removed to a low level such as 0.5 weight %, or lower, depending upon the application of the polymer. In some embodiments of the present invention, the method involves producing a polymer with residual solvent or obtaining a polymer with residual solvent. The residual solvent level of the polymer or polymer construct prior to the initiation of a subsequent processing operation may range from not less than 0.1% by weight, to not more than 20% by weight. In some embodiments, the residual solvent level is at least 1%, at least 2%, at least 3%, at least 4%, but not more than 15% by weight. In some embodiments, the residual solvent level is 5%, but not more than 15% by weight. Some non-limiting examples of solvents that may be used, individually or in combination with one or more of the others, and/or one or more other solvents, in solvent processing of the bioabsorbable polymer, poly(L-lactide), or a copolymer with a constitutional unit derived from L-lactic, include acetone, 2-butanone, 1,1,2 trichloroethylene (TCE), methylene chloride, chloroform, tetrahydrofuran, dioxane, and dimethyl acetamide.

In some embodiments, the removal of the residual solvent occurs during, after, or both during and after a subsequent processing operation in which the polymer is heated to and maintained at a temperature between the glass transition temperature and an upper temperature. The temperature may fluctuate or vary during the subsequent processing operation. Examples of such operations include axial extension, radial expansion, a combination of radial expansion and axial extension, or annealing at constant diameter, constant length, or both.

In some embodiments, at least 80 weight %, at least 85 weight %, at least 90 weight %, at least 95 weight %, at least 97 weight %, at least 98 weight %, at least 99 weight %, or at least 99.5 weight % of the residual solvent is removed during the execution of subsequent processing operation such as, without limitation, radial expansion. In some embodiments not more than 20 weight %, not more than 15 weight %, or not more than 10 weight % of the solvent is removed during the subsequent processing operation. As noted previously, the residual solvent may act as a plasticizer. The plasticization may allow processing at a lower temperature. In some embodiments, after the execution of the subsequent processing operation, the polymer may include at least 60 weight %, at least 70%, at least 80 weight %, at least 90 weight %, at least 95%, at least 98 weight %, or at least 99 weight % of the residual solvent. The remaining residual solvent may be removed (or at least 90 weight %, at least 95 weight %, or at least 98 weight % of the remaining residual solvent) after the execution of the subsequent processing operation, but prior to additional processing operations, if any are executed, and packaging. Residual solvent may be removed to an acceptable level prior to initiation of packaging, or prior to applying a drug coating.

In other embodiments, a polymer tube or polymer construct is provided (or formed by another process, such as but not limited to, a solvent based process) and exposed to solvent vapor under conditions such that the polymer absorbs the solvent prior to the execution of a processing operation in which the polymer is heated to a temperature between the glass transition temperature and an upper temperature. The polymer tube or polymer construct may have an inherent viscosity of at least 3.3 dl/g, but not more than 15 dl/g. The conditions are exposure for a sufficient time to the solvent vapor, the solvent vapor being at a sufficient vapor pressure during that time to reach at least 0.01 weight % solvent in the polymer. As used herein, with reference to exposing a polymer to a solvent vapor in order for the polymer to absorb the solvent, a solvent will refer to a substance, including a fluid, that plasticizes, swells, or both plasticizes and swells the polymer. In preferred embodiments, the solvent chosen would be a good solvent for the polymer (where a "good" solvent is a solvent in which polymer-solvent interactions are stronger than polymer-polymer interactions or solvent-solvent interactions), or at least a solvent that can partially swell the polymer (at least 0.01 weight % absorption of solvent, preferably at least 0.1 weight % absorption of solvent). As a non-limiting example, if the polymer is poly(L-lactide) (PLLA), or a copolymer with constitutional units derived from L-lactic acid, the solvent may be acetone, a chlorinated solvent, such as without limitation methylene chloride or chloroform, or tetrahydrofuran.

The polymer may be exposed to a solvent or solvent vapor in order for the polymer to absorb the solvent where the solvent may be different from any solvent used in production of the polymer, and may be different from any solvent used in post-production processing of the polymer. In some embodiments, the solvent may be different from a solvent used in the immediately preceding processing operation. In some embodiments, the solvent is different from any one or more members of the group of methylene chloride, acetone, 2-butanone, trichloroethylene, chloroform, dimethylacetamide, cyclohexanone, tetrahydrofuran, and dioxane.

The amount of solvent absorbed by the polymer may be in the range of 0.01 weight % to 20 weight %, preferably 0.02 weight % to 15 weight %, more preferably 0.1 weight % to 12 weight %, and even more preferably 0.2 weight % to 10 weight %. In some embodiments, amount of solvent absorbed by the polymer may be in the range of 0.1% to 8 weight %, 2 weight % to 15 weight %, or 5 weight % to 30 weight %. In some embodiments, a sufficient amount of solvent is absorbed to lower the glass transition temperature of the polymer by at least 5° C., by at least 10° C., by at least 15° C., or by at least 20° C., but not more than 75° C. In some embodiments, the amount of solvent absorbed by the polymer, in the range of 0.1 weight % to 35 weight %, lowers the glass transition temperature by 5° C. to 50° C., or 10° C. to 40° C.

In some embodiments, there may be a combination of residual solvent and absorbed solvent which acts as a plasticizer. In some embodiments, the absorbed solvent is the same solvent as the residual solvent. In some embodiments, the absorbed solvent is a different solvent than the residual solvent.

In some embodiments, the combination of the residual solvent and absorbed solvent may be in the range of 0.01 weight % to 20 weight %, preferably 0.02 weight % to 15 weight %, more preferably 0.1 weight % to 12 weight %, and even more preferably 0.2 weight % to 10 weight %. In some embodiments, amount of solvent absorbed by the polymer in combination with the residual solvent may be in the range of 0.1% to 8 weight %, 2 weight % to 15 weight %, or 5 weight % to 30 weight %. In some embodiments, a sufficient amount of solvent is absorbed such that in combination with the residual solvent, the glass transition temperature of the polymer is decreased by at least 5° C., by at least 10° C., by at least 15° C., or by at least 20° C., but not more than 75° C. In some embodiments, the amount of solvent absorbed by the polymer, in the range of 0.1 weight % to 35 weight %, lowers the glass transition temperature by 5° C. to 50° C., or 10° C. to 40° C.

A sufficient time may range from 2 minutes to 480 minutes, preferably 5 minutes to 360 minutes, and even more preferably 10 minutes to 240 minutes. During this time, the solvent vapor may be at a sufficient vapor partial pressure such as without limitation, at least 25% of the pure solvent vapor pressure at the temperature of the operation, preferably at least 50%, and more preferably at least 75%. In some embodiments, the solvent is above its boiling point, and a solvent above its boiling point is sufficient if at a partial pressure of not less than 20 Torr.

In some embodiments in which the polymer has a residual solvent content from prior processing operations, the polymer construct has been exposed to a solvent vapor to absorb solvent into the polymer, or both, the polymer may be exposed to solvent vapor of at least 25% of the value of the pure solvent vapor pressure at that temperature during a processing operation in which the polymer is heated to a temperature between the glass transition temperature and an upper temperature. As an example, for a polymer tube that is subject to radial expansion, axial extension, or both, the tube may be exposed to solvent vapor during at least part of the time period of the execution of the operation comprising expansion, extension, or both. In some embodiments, the solvent vapor pressure may be sufficiently high to prevent desorption or removal of the solvent that is already absorbed into the polymer. As a non-limiting example, solvent vapor may be passed through the interior of a tube during the operation comprising radial expansion, axial extension, or both. In some embodiments, the solvent vapor partial pressure or amount of solvent in the environment is sufficiently high (at least 25% of the vapor pressure of the pure solvent at the temperature of the environment) to limit desorption of the absorbed solvent, residual solvent, or both, to not more than 20%, not more than 30%, or not more than 50% by weight.

The removal of the residual solvent, absorbed solvent, or both, may be accomplished by the same heating and maintaining methods disclosed above that are used for the removal of plasticizer. In other words, the heating and maintaining whether under a vacuum, at normal atmospheric pressure, in the present of high humidity, or in the present of a solvent vapor different from the absorbed solvent, or a combination thereof, is executed to remove solvent.

In preferred embodiments, the polymer used in the various embodiments of the present invention described herein may be Poly(L-lactide) (PLLA), a polymer with constitutional units derived from L-lactic acid being at least 30 mol %, preferably, at least 50 mol %, more preferably 60 mol %, and even more preferably at least 70 mol %, and up to 98 mol %, a copolymer with at least 75 weight % being constitutional units derived from L-lactic acid, a copolymer with at least 80 weight % being constitutional units derived from L-lactic acid, a copolymer with at least 85 weight % being constitutional units derived from L-lactic acid, or a combination thereof. In preferred embodiments, the polymer may be poly(L-lactide-co-glycolide), poly(D,L-lactide-co-L-lactide), poly(L-lactide-co-caprolactone), or a combination thereof with at least 60 mol % being constitutional units derived from L-lactic acid. Blends of poly(L-lactide) with the copolymer poly(L-lactide-co-caprolactone) are also possible. Poly(L-lactide) (PLLA) is attractive as a stent material due to its relatively high strength and a rigidity at human body temperature, about 37° C. The glass transition temperature (Tg) of PLLA varies between approximately 50 to 80° C., or more narrowly between 55 and 65° C., depending on crystallinity, microstructure, and molecular weight. Since typically, PLLA has glass transition temperature between about 60 and 65° C. (Medical Plastics and Biomaterials Magazine, March 1998), it remains stiff and rigid at human body temperature. This property facilitates the ability of a stent to maintain a lumen at or near a deployed diameter without significant recoil. In some embodiments, the polymer may be a polymer of a constitutional unit derived from L-lactic acid, glycolic acid, or a combination thereof, and optionally including other constitutional units, and with a glass transition temperature of at least 28° C., preferably at least 30° C., and in some embodiments, a glass transition temperature of at least 37° C., or at least 37° C. when saturated with water at 37° C.

In some embodiments, the stent body is formed of a polymer blended or mixed with an absorbable metal, for example magnesium, or an absorbable glass, such as iron doped absorbable glass.

The stent can further include a coating of one or multiple layers disposed over the body or scaffolding having dimension of about 30 angstroms to 20 microns, preferably 30 angstroms to 10 microns, and more preferably 150 angstroms to 5 microns. The coating may be free of drugs, or may include a drug. In one embodiment, the coating may be a polymer and drug mixture, which may be called a drug reservoir layer. There may be multiple drug reservoir layers. One or more layers may be below the drug reservoir layer, above the drug reservoir layer, or both, and this applies to each drug reservoir layer in the coating. In sum, there be any number of coating layers, each of which may or may not contain a drug. For example, the coating can be poly(D,L-lactide) and the drug could be an antiproliferative, such as everolimus. The coating can be free of other materials other than incidental migration or diffusion of other materials form the body of the device into the coating, and/or from one layer of the coating into another. In some embodiments, materials from the packaging may diffuse or migrate into the coating and/or body of the device.

Other drugs may be used in a coating over the device body, within the device body, or a combination thereof. Drugs may be used individually or in combination. Drugs that may be suitable for use in the embodiments of the present invention, depending, of course, on the specific disease being treated, include, without limitation, anti-restenosis, pro- or anti-proliferative, anti-inflammatory, antineoplastic, antimitotic, anti-platelet, anticoagulant, antifibrin, antithrombin, cytostatic, antibiotic, anti-enzymatic, anti-metabolic, angiogenic, cytoprotective, angiotensin converting enzyme (ACE) inhibiting, angiotensin II receptor antagonizing, and cardioprotective drugs. Some drugs may fall into more than one category.

The term "anti-proliferative" as used herein, refers to a therapeutic agent that works to block the proliferative phase of acute cellular rejection. The anti-proliferative drug can be a natural proteineous substance such as a cytotoxin or a synthetic molecule. Other drugs include, without limitation, anti-proliferative substances such as actinomycin D, and derivatives thereof (manufactured by Sigma-Aldrich 1001 West Saint Paul Avenue, Milwaukee, Wis. 53233; or COSMEGEN™ available from Merck) (synonyms of actinomycin D include dactinomycin, actinomycin IV, actinomycin I1, actinomycin X1, and actinomycin C1), all taxoids such as taxols, docetaxel, paclitaxel, and paclitaxel derivatives, FKBP-12 mediated mTOR inhibitors, and pirfenidone. Other anti-proliferative drugs include rapamycin (sirolimus), everolimus, zotarolimus (ABT-578), biolimus A9, ridaforolimus (formerly deforolimus, and also known as AP23573), tacrolimus, temsirolimus, pimecrolimus, novolimus, myolimus, umirolimus, merilimus, 40-O-(3-hydroxypropyl)rapamycin, 40-O-[2-(2-hydroxy)ethoxy]ethyl-rapamycin, 40-O-tetrazolylrapamycin, and 40-epi-(N1-tetrazolyl)-rapamycin. Other compounds that may be used as drugs are compounds having the structure of rapamycin but with a substituent at the carbon corresponding to the 42 or 40 carbon (see structure below).

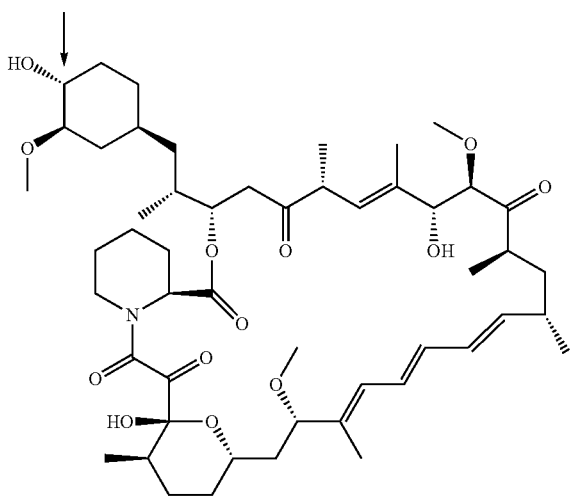

Rapamycin

Additional examples of cytostatic or antiproliferative drugs include, without limitation, angiopeptin, and fibroblast growth factor (FGF) antagonists.

Examples of anti-inflammatory drugs include both steroidal and non-steroidal (NSAID) anti-inflammatories such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone dipropionate, dexamethasone acetate, dexamethasone phosphate, mometasone, cortisone, cortisone acetate, hydrocortisone, prednisone, prednisone acetate, betamethasone, betamethasone acetate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus and pimecrolimus.

Alternatively, the anti-inflammatory drug can be a biological inhibitor of pro-inflammatory signaling molecules. Anti-inflammatory drugs may be bioactive substances including antibodies to such biological inflammatory signaling molecules.

Examples of antineoplastics and antimitotics include, without limitation, paclitaxel, docetaxel, methotrexate, azathioprine, vincristine, vinblastine, fluorouracil, doxorubicin hydrochloride and mitomycin.

Examples of anti-platelet, anticoagulant, antifibrin, and antithrombin drugs include, without limitation, heparin, sodium heparin, low molecular weight heparins, heparinoids, hirudin, argatroban, forskolin, vapiprost, prostacyclin, prostacyclin dextran, D-phe-pro-arg-chloromethylketone, dipyridamole, glycoprotein IIb/IIIa platelet membrane receptor antagonist antibody, recombinant hirudin and thrombin, thrombin inhibitors such as ANGIOMAX® (bivalirudin), calcium channel blockers such as nifedipine, colchicine, fish oil (omega 3-fatty acid), histamine antagonists, lovastatin, monoclonal antibodies such as those specific for Platelet-Derived Growth Factor (PDGF) receptors, nitroprusside, phosphodiesterase inhibitors, prostaglandin inhibitors, suramin, serotonin blockers, steroids, thioprotease inhibitors, triazolopyrimidine, nitric oxide, nitric oxide donors, super oxide dismutases, super oxide dismutase mimetic and 4-amino-2,2,6,6-tetramethylpiperidine-1-oxyl (4-amino-TEMPO).

Examples of ACE inhibitors include, without limitation, quinapril, perindopril, ramipril, captopril, benazepril, trandolapril, fosinopril, lisinopril, moexipril and enalapril.

Examples of angiotensin II receptor antagonists include, without limitation, irbesartan and losartan.

Other drugs that may be used, include, without limitation, estradiol, 17-beta-estradiol, γ-hiridun, imatinib mesylate, midostaurin, feno fibrate, and feno fibric acid.

Other drugs that have not been specifically listed may also be used. Some drugs may fall into more than one of the above mentioned categories. Prodrugs thereof, co-drugs thereof, and combinations thereof of the above listed drugs are also encompassed in the various embodiments of the present invention.

Representative examples of polymers, oligomers, and materials that may be used, individually or in combination, in the coatings described herein, and optionally, may be used, individually or in combination with any other materials described herein, in forming a device body, include, without limitation, polyesters, polyhydroxyalkanoates, poly (3-hydroxyvalerate), poly(lactide-co-glycolide), poly(3-hydroxybutyrate), poly(4-hydroxybutyrate), poly(3-hydroxybutyrate-co-3-hydroxyvalerate), polyhydroxybutyrate, polyhydroxybutyrate-co-hydroxyvalerates, polyhydroxybutyrate-co-hydroxyhexanoate, polyorthoesters, polyanhydrides, poly(glycolic acid), poly(glycolide), poly(L-lactic acid), poly(L-lactide), poly(D,L-lactic acid), poly(D,L-lactide), poly(L-lactide-co-D,L-lactide), poly(caprolactone), poly(L-lactide-co-caprolactone), poly(D,L-lactide-co-caprolactone), poly(D-lactide-co-caprolactone), poly(D-lactide), poly(glycolide-co-caprolactone), poly(trimethylene carbonate), polyester amides, poly(glycolic acid-co-trimethylene carbonate), poly(amino acid)s, polyphosphazenes, polycarbonates, cellulose acetate, cellulose butyrate, cellulose acetate butyrate, cellophane, cellulose nitrate, cellulose propionate, cellulose ethers, silk-elastin, elastin mimetic peptides, alginic acid, alginate, chondroitin sulfate, chitosan, chitosan sulfate, collagen, fibrin, fibrinogen, cellulose, cellulose sulfate, carboxymethylcellulose, hydroxyl cellulose, hydroxypropyl cellulose, hydroxypropyl methylcellulose (HPMC), carboxymethylcellulose sodium, hydroxyethylcellulose, gelatin, sugars, starch, modified starches, such as hydroxyethyl starch and 2-O-acetyl starches), polysaccharides, dextran sulfate, dextran, dextrin, xanthan, hyaluronic acid, fragments of hyaluronic acid, polysaccharides, and copolymers thereof.

As used herein, the terms poly(D,L-lactide), poly(L-lactide), poly(D,L-lactide-co-glycolide), and poly(L-lactide-co-glycolide) are used interchangeably with the terms poly (D,L-lactic acid), poly(L-lactic acid), poly(D,L-lactic acid-co-glycolic acid), and poly(L-lactic acid-co-glycolic acid), respectively.

As used herein, caprolactone includes, but is not limited to, 6-caprolactone.

For the purposes of the present invention, the following terms and definitions apply:

"Compression molding" is a method of molding in which the molding material, generally preheated, is first placed in an open, heated mold cavity. The mold is closed with a top force or plug member, pressure is applied to force the material into contact with all mold areas, and heat and pressure are maintained until the molding material has cured. The process may employ thermosetting resins in a partially cured stage, either in the form of granules, putty-like masses, or preforms. A polymer construct may be formed by compression molding.

"Ram extrusion" refers to a process in which a resin is fed from a hopper and packed into a cylinder in repeated increments by a reciprocating plunger. The frequency and amplitude of the plunger stroke can be controlled by an oil hydraulic system. The compressed material moves through a heated zone where it is fused into a profile matching the cross section of the barrel or die. The output rate is proportional to the length and frequency of the ram strokes. Die length, electrical heater capacity, hydraulic system power and maximum force, and the strength of the construction materials determine equipment capability.

"Gel extrusion", also known as phase separation or extraction or wet process, is a process in which a polymer fluid, including a polymer mixed with a solvent, is extruded. The polymer has a viscosity low enough to be extruded at temperatures below the melting point of the polymer.

As used herein, a "polymer" refers to a molecule comprised of, actually or conceptually, repeating "constitutional units." The constitutional units derive from the reaction of monomers. As a non-limiting example, ethylene ($CH_2$=$CH_2$) is a monomer that can be polymerized to form polyethylene, $CH_3CH_2(CH_2CH_2)_nCH_2CH_3$ (where n is an integer), wherein the constitutional unit is —$CH_2CH_2$—, ethylene having lost the double bond as the result of the polymerization reaction. Although poly(ethylene) is formed by the polymerization of ethylene, it may be conceptually thought of being comprised of the —$CH_2$— repeating unit, and thus conceptually the polymer could be expressed by the formula $CH_3(CH_2)_mCH_3$ where m is an integer, which would be equal to 2n+2 for the equivalent number of ethylene units reacted to form the polymer. A polymer may be derived from the polymerization of two or more different monomers and therefore may comprise two or more different constitutional units. Such polymers are referred to as "copolymers." "Terpolymers" are a subset of "copolymers" in which there are three different constitutional units. The constitutional units themselves can be the product of the reactions of other compounds. Those skilled in the art, given a particular polymer, will readily recognize the constitutional units of that polymer and will equally readily recognize the structure of the monomer or materials from which the constitutional units derive. Polymers may be straight or branched chain, star-like or dendritic, or one polymer may be attached (grafted) onto another. Polymers may have a random disposition of constitutional units along the chain, the constitutional units may be present as discrete blocks, or constitutional units may be so disposed as to form gradients of concentration along the polymer chain. Polymers may be cross-linked to form a network.

As used herein, a polymer has a chain length of 50 constitutional units or more, and those compounds with a chain length of fewer than 50 constitutional units are referred to as "oligomers." As used to differentiate between oligomers and polymers herein, the constitutional unit will be the smallest unique repeating unit. For example, for poly(lactide) the constitutional unit would be

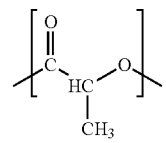

even though the polymer may be formed by the reaction of the cyclical dimer, lactide,

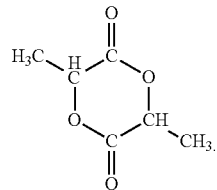

Similarly, for poly(ethylene) the constitutional unit used to count the "number" of constitutional units would be the number of —$CH_2$— units, even though conventionally the constitutional unit is stated to be —$CH_2CH_2$— because it is always derived from the reaction of ethylene.

"Molecular weight" can refer to the molecular weight of individual segments, blocks, or polymer chains. "Molecular weight" can also refer to weight average molecular weight or number average molecular weight of types of segments, blocks, or polymer chains.

The number average molecular weight ($M_n$) is the common, mean, average of the molecular weights of the individual segments, blocks, or polymer chains. It is determined by measuring the molecular weight of N polymer molecules, summing the weights, and dividing by N:

$$M_n = \frac{\sum_i N_i M_i}{\sum_i N_i}$$

where $N_i$ is the number of polymer molecules with molecular weight $M_i$. The weight average molecular weight is given by:

$$M_w = \frac{\sum_i N_i M_i^2}{\sum_i N_i M_i}$$

where $N_i$ is the number of molecules of molecular weight $M_i$. Another commonly used molecular weight average is the viscosity average molecular weight which may be express as:

$$M_v = \left[\frac{\sum_i M_i^{(1+a)} N_i}{\sum_i M_i N_i}\right]^{1/a}$$

where a is typically less than 1, and is related to intrinsic viscosity.

The "inherent viscosity" (of a polymer) is the ratio of the natural logarithm of the relative viscosity, ηr, to the mass concentration of the polymer, c, i.e. ηinh=(ln ηr)/c, where the relative viscosity (ηr) is the ratio of the viscosity of a polymer solution, η, to the viscosity of the solvent (ηs), ηr=η/ηs.

The "glass transition temperature," $T_g$, is the temperature at which the amorphous domains of a polymer change from a brittle, vitreous state to a solid deformable state (or rubbery state) at atmospheric pressure. In other words, the $T_g$ corresponds to the temperature where the onset of segmental motion in the chains of the polymer occurs. The measured $T_g$ of a given polymer can be dependent on the heating rate and can be influenced by the thermal history, and potentially pressure history, of the polymer, as well as potentially the pressure at which the measurement is made. $T_g$ is also affected by other compounds mixed with the polymer, such as, without limitation, fillers, or residual solvent, etc. The chemical structure of the polymer heavily influences the glass transition by affecting mobility. As used herein the glass transition temperature of the polymer will refer to the glass transition temperature of the polymer as measured by standard differential scanning calorimetry (modulated or unmodulated) with a temperature ramp of 5-20° C./min and if modulated, with a temperature modulation of 0.01 to 2° C. with a modulation period of 1 to 100 seconds, utilizing nitrogen or argon at a flow rate of 5-200 ml/min.

The "melting temperature," Tm, of a polymer is the temperature at which an endothermal peak is observed in a DSC measurement, and where at least some of the crystallites begin to become disordered. The measured melting temperature may occur over a temperature range as the size of the crystallites, as well as presence of impurities, plasticizers, or a combination thereof, impacts the measured melting temperature of a polymer.

As used herein, a reference to the crystallinity of a polymer refers to the crystallinity as determined by standard DSC techniques.

Plasticization refers to the addition of a second, lower $T_g$ substance, which is generally lower molecular weight material, to a polymer where the substance is at least partially miscible with the polymer. The effect is to lower the $T_g$ of the blend, and generally, also to transform a hard, brittle material to a soft, rubber-like material. According to the free volume model, the plasticizer, that is the second lower $T_g$ and generally lower molecular weight material, added to the polymer, has a higher free volume. The addition of a higher free volume material to the polymer increases the "free volume" of the blend, and allows for greater polymer chain mobility, thus lowering the $T_g$. An alternative view, based on a lattice model similar to that used by Flory and Huggins, is that the true thermodynamic $T_g$ is the point of zero configurational entropy. Thus, in this model, the lower $T_g$ resulting from the addition of a second smaller molecule is due to the larger number of potential configurations of the polymer chains with the presence of the smaller molecule when compared to the number of potential configurations with only the long chain polymer molecules. Thus, regardless of the theoretical explanation for plasticization, the uptake of a plasticizer would tend to allow for greater polymer chain mobility, and as a result, a lower $T_g$.

"Stress" refers to force per unit area, as in the force acting through a small area within a plane. Stress can be divided into components, normal and parallel to the plane, called normal stress and shear stress, respectively. True stress denotes the stress where force and area are measured at the same time. Conventional or engineering stress, as applied to tension and compression tests, is force divided by the original gauge length.

"Strength" refers to the maximum stress along an axis which a material will withstand prior to fracture. The ultimate strength is calculated from the maximum load applied during the test divided by the original cross-sectional area.

"Radial strength" of a stent is defined as the pressure at which a stent experiences irrecoverable deformation. The loss of radial strength is followed by a gradual decline of mechanical integrity.

"Modulus" may be defined as the ratio of a component of stress or force per unit area applied to a material divided by the strain along an axis of applied force that results from the applied force. The modulus is the initial slope of a stress-strain curve, and therefore, determined by the linear hookean region of the curve. For example, a material has a tensile, a compressive, and a shear modulus.

"Strain" refers to the amount of elongation or compression that occurs in a material at a given stress or load, or in other words, the amount of deformation.

"Elongation" may be defined as the increase in length in a material which occurs when subjected to stress. It is typically expressed as a percentage of the original length.

"Toughness" is the amount of energy absorbed prior to fracture, or equivalently, the amount of work required to fracture a material. One measure of toughness is the area under a stress-strain curve from zero strain to the strain at fracture. The units of toughness in this case are in energy per unit volume of material. See, e.g., L. H. Van Vlack, "Elements of Materials Science and Engineering," pp. 270-271, Addison-Wesley (Reading, Pa., 1989).

As used herein, a "drug" refers to a substance that, when administered in a therapeutically effective amount to a patient suffering from a disease or condition, has a therapeutic beneficial effect on the health and well-being of the patient. A therapeutic beneficial effect on the health and well-being of a patient includes, but is not limited to, any one or more of the following: (1) curing the disease or condition; (2) slowing the progress of the disease or condition; (3) causing the disease or condition to retrogress; (4) alleviating one or more symptoms of the disease or condition.

As used herein, a "drug" also includes any substance that when administered to a patient, known or suspected of being particularly susceptible to a disease, in a prophylactically effective amount, has a prophylactic beneficial effect on the health and well-being of the patient. A prophylactic beneficial effect on the health and well-being of a patient includes, but is not limited to, any one or more of the following: (1) preventing or delaying on-set of the disease or condition in the first place; (2) maintaining a disease or condition at a retrogressed level once such level has been achieved by a therapeutically effective amount of a substance, which may be the same as or different from the substance used in a prophylactically effective amount; (3) preventing or delaying recurrence of the disease or condition after a course of treatment with a therapeutically effective amount of a substance, which may be the same as or different from the substance used in a prophylactically effective amount, has concluded.

As used herein, "drug" also refers to pharmaceutically acceptable, pharmacologically active salts, esters, amides, and the like, of those drugs specifically mentioned herein.

As used herein, a material that is described as "disposed over" an indicated substrate refers to, e.g., a coating layer of the material deposited directly or indirectly over at least a portion of the surface of the substrate. Direct depositing means that the coating layer is applied directly to the surface of the substrate. Indirect depositing means that the coating layer is applied to an intervening layer that has been deposited directly or indirectly over the substrate. A coating layer is supported by a surface of the substrate, whether the coating layer is deposited directly, or indirectly, onto the surface of the substrate. The terms "layer" and "coating layer" will be used interchangeably herein. A "layer" or "coating layer" of a given material is a region of that material whose thickness is small compared to both its length and width (e.g., the length and width dimensions may both be at least 5, 10, 20, 50, 100 or more times the thickness dimension in some embodiments). As used herein a layer need not be planar, for example, taking on the contours of an underlying substrate. Coating layers can be discontinuous. As used herein, the term "coating" refers to one or more layers deposited on a substrate. A coating layer may cover all of the substrate or a portion of the substrate, for example a portion of a medical device surface. Typically, a coating layer does not provide a significant fraction of the mechanical support for the device. In some embodiments, the layers differ from one another in the type of materials in the layer, the proportions of materials in the layer, or both. In some embodiments, a layer may have a concentration gradient of the components. One of skill in the art will be able to differentiate different coating layers or regions from each other based on the disclosure herein.

As used herein, "above" a surface or layer is defined as further from the substrate measured along an axis normal to a surface, or over a surface or layer, but not necessarily in contact with the surface or layer.

As used herein, "below" a surface or layer is defined as closer to the substrate measured along an axis normal to a surface, or under a surface or layer, but not necessarily in contact with the surface or layer.

While particular embodiments of the present invention have been shown and described, it will be obvious to those skilled in the art that changes and modifications can be made without departing from this invention in its broader aspects. Therefore, the claims are to encompass within their scope all such changes and modifications as fall within the true spirit and scope of this invention. Moreover, although individual aspects or features may have been presented with respect to one embodiment, a recitation of an aspect for one embodiment, or the recitation of an aspect in general, is intended to disclose its use in all embodiments in which that aspect or feature can be incorporated without undue experimentation. Also, embodiments of the present invention specifically encompass embodiments resulting from treating any dependent claim which follows as alternatively written in a multiple dependent form from all prior claims which possess all antecedents referenced in such dependent claim (e.g. each claim depending directly from claim 1 should be alternatively taken as depending from any previous claims).

What is claimed is:

1. A method of fabricating a medical device, the method comprising:

processing a polymer to form a medical device or a polymer construct, the processing occurring at a high temperature, the high temperature being above the melting temperature of the polymer, if the polymer exhibits a melting temperature above 35° C., or if the polymer does not exhibit a melting temperature above 35° C., at a temperature higher than 100° C. above the glass transition temperature (Tg) of the polymer, or higher than 75° C., if 75° C. is greater than 100° C. above the Tg of the polymer;

adding a plasticizer to the polymer prior to, during, or both prior to and during the processing of the polymer; wherein the plasticizer is different from any solvent used in production of the polymer;

removing at least 75 weight % of the plasticizer from the processed polymer, the removal comprising heating the processed polymer to and maintaining the processed polymer at a temperature above the glass transition temperature of the polymer or above 28° C., if the glass transition temperature of the polymer is lower than 25° C., and below the melting temperature of the polymer, if the polymer has a melting temperature above 28° C., or if the polymer does not have a melting temperature above 28° C., below the temperature that is 75° C. greater than the glass transition temperature of the polymer, or below 60° C., if 60° C. is higher than 75° C. greater than the glass transition temperature of the polymer;

optionally executing one or more additional processing operations on the medical device or on the polymer construct;

wherein the polymer has a number average molecular weight as measured by GPC using polystyrene standards of at least 250,000 g/mole, but not more than 3,000,000 g/mole, the polymer has a weight average molecular weight of at least 300,000 g/mole but not more than 4,500,000 g/mole, an inherent viscosity of at least 3.3 dl/g, but not more than 15 dl/g, or a combination thereof;

wherein the polymer that is processed optionally comprises another material in addition to the plasticizer; and wherein if the polymer construct is formed, at least one additional processing operation is executed to form a medical device from the polymer construct.

2. The method of claim 1, wherein the plasticizer is added at a weight ratio of plasticizer to polymer of about 1/1000 to 1/10.

3. The method of claim 1, wherein the processing of the polymer at the high temperature comprises extrusion, injection molding, or a combination thereof.

4. The method of claim 1, wherein at least one of the one or more additional processing operations is executed, the at least one additional processing operation comprising heating the polymer to a temperature above the glass transition temperature of the polymer or above 28° C., if the glass transition temperature of the polymer is lower than 25° C., and below the melting temperature of the polymer, if the polymer has a melting temperature above 28° C., or if the polymer does not have a melting temperature above 28° C., below the temperature that is 75° C. greater than the glass transition temperature of the polymer, or below 60° C., if 60° C. is higher than 75° C. greater than the glass transition temperature of the polymer.

5. The method of claim 1, wherein the processing of the polymer at the high temperature comprises extrusion, injection molding, or a combination thereof to form the polymer construct, the polymer construct being a polymer tube, and wherein at least one of the one or more additional processing operations is executed, the at least one additional processing operation comprising axial expansion of the polymer tube, radial expansion of the polymer tube, or a combination of radial and axial expansion of the polymer tube after the polymer tube has been heated to a temperature above the glass transition temperature of the polymer or above 28° C., if the glass transition temperature of the polymer is lower than 25° C., and below the melting temperature of the polymer, if the polymer has a melting temperature above 28° C., or if the polymer does not have a melting temperature above 28° C., below the temperature that is 75° C. greater than the glass transition temperature of the polymer, or below 60° C., if 60° C. is higher than 75° C. greater than the glass transition temperature of the polymer of the polymer tube.

6. The method of claim 5, additionally comprising forming a pattern in the tube to form the medical device.

7. The method of claim 1, wherein the plasticizer is selected from the group consisting of citrate ester, phthalate esters, C1 to C16 esters of $\alpha$-hydroxy acids, oligomers of up to 10 units of $\alpha$-hydroxy acids, C1 to C16 esters of these oligomers of $\alpha$-hydroxy acids, and combinations thereof.

8. The method of claim 1, wherein the removal of at least 90 weight % of the plasticizer is executed prior to the medical device being packaged.

9. The method of claim 8, wherein at least one of the one or more additional processing operations is executed, the at least one additional processing operation comprising heating the polymer to a temperature above the glass transition temperature of the polymer or above 28° C., if the glass transition temperature of the polymer is lower than 25° C., and below the melting temperature of the polymer, if the polymer has a melting temperature above 28° C., or if the polymer does not have a melting temperature above 28° C., below the temperature that is 75° C. greater than the glass transition temperature of the polymer, or below 60° C., if 60° C. is higher than 75° C. greater than the glass transition temperature of the polymer; and wherein the plasticizer is removed during, after, or both during and after the at least one additional processing operation.

10. The method of claim 9, wherein the processing of the polymer at the high temperature comprises extrusion, injection molding, or a combination thereof to form a polymer tube, and wherein the at least one additional processing operation further comprises axial expansion of the polymer tube, radial expansion of the polymer tube, or a combination of radial and axial expansion of the polymer tube after the polymer tube has been heated to a temperature above the glass transition temperature of the polymer or above 28° C., if the glass transition temperature of the polymer is lower than 25° C., and below the melting temperature of the polymer, if the polymer has a melting temperature above 28° C., or if the polymer does not have a melting temperature above 28° C., below the temperature that is 75° C. greater than the glass transition temperature of the polymer, or below 60° C., if 60° C. is higher than 75° C. greater than the glass transition temperature of the polymer of the polymer tube.

11. The method of claim 10, additionally comprising forming a pattern in the tube to form the medical device.

12. The method of claim 1, wherein the heating and maintaining occurs at a pressure below 200 Torr.

13. The method of claim 1, wherein the heating and maintaining occurs in an environment with a humidity of at least 40% rh and not more than 99% rh.

14. The method of claim 1, wherein during the heating and maintaining, the polymer is exposed to solvent vapor of at least 20 Torr partial pressure wherein the solvent is a good solvent for the plasticizer.

15. The method of claim 14, wherein the solvent at least partially plasticizes the polymer.

16. The method of claim 14, wherein the partial pressure of the solvent vapor is at least 200 Torr.

17. The method of claim 14, wherein for a duration of at least 2 minutes the polymer is exposed to a partial pressure of the solvent vapor of at least 20 Torr.

18. The method of claim 14, wherein after the heating and maintaining in the presence of solvent vapor is complete, the polymer is additionally maintained at the temperature of the heating and maintaining without solvent vapor present or with less than 100 ppm solvent vapor present for a duration of time of not less than 5 minutes.

19. The method of claim 1, wherein the plasticizer is N-methyl pyrrolidone, isophorone, butyl benzoate, ethyl benzoate, sulfolane, or a combination thereof.

* * * * *